United States Patent
Chadeayne

(10) Patent No.: US 11,858,896 B2
(45) Date of Patent: Jan. 2, 2024

(54) CRYSTALLINE DIMETHYL TRYPTAMINE ANALOGUES

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 67 days.

(21) Appl. No.: 17/997,413

(22) PCT Filed: May 4, 2021

(86) PCT No.: PCT/US2021/030597
§ 371 (c)(1),
(2) Date: Oct. 28, 2022

(87) PCT Pub. No.: WO2021/226041
PCT Pub. Date: Nov. 11, 2021

(65) Prior Publication Data
US 2023/0150937 A1    May 18, 2023

Related U.S. Application Data

(60) Provisional application No. 63/019,579, filed on May 4, 2020.

(51) Int. Cl.
C07D 209/16    (2006.01)

(52) U.S. Cl.
CPC ........ *C07D 209/16* (2013.01); *C07B 2200/13* (2013.01)

(58) Field of Classification Search
CPC .................................................. C07D 209/16
See application file for complete search history.

(56) References Cited

U.S. PATENT DOCUMENTS

| | | |
|---|---|---|
| 2018/0021326 A1 | 1/2018 | Stamets |
| 2018/0221396 A1 | 8/2018 | Chadeayne |
| 2019/0142851 A1 | 5/2019 | Chadeayne |

FOREIGN PATENT DOCUMENTS

WO   2021/041407 A1   3/2021

OTHER PUBLICATIONS

International Search Report and Written Opinion in International Application No. PCT/US2021/030597 dated Aug. 6, 2021.
Gupta et al.'Salts of Therapeutic Agents: Chemical, Physicochemical, and Biological Considerations' Molecules, 2018, vol. 23, entirety of document especially Abstract; p. 2 para 1-3; Table 1.
Wikipedia 'Fumaric acid' Jan. 13, 2020 (Jan. 13, 2020) retrieved from <https://en. wikipedia.org/w/index.php?title=Fumaric_acid &oldid=935516441 > entirety of document especially p. 1 para 1; Table 1.
Wikipedia 'Dementia' Sep. 22, 2019 (Sep. 22, 2019) retrieved from <https://en.wikipedia.org/w/index.php?title=Dementia&oldid= 917048749> entirety of document especially p. 4 para 1-3.
Ascic, E., Hansen, C. L., Le Quement, S. T. & Nielsen, T. E. (2012). Chem. Commun., 48, 3345-3347.
Blei, F., Dorner, S., Fricke, J., Baldeweg, F., Trottmann, F., Komar, A., Meyer, F., Hertweck, C. & Hoffmeister, D. (2020). Chem. Eur. J., 26, 729-734.
Brandt, S. D., Freeman, S., Fleet, I. A. & Alder, J. F. (2005b). Analyst, 130, 1258-1262.
Brandt, S. D., Freeman, S., Fleet, I. A., McGagh, P. & Alder, J. F. (2005a). Analyst, 130, 330-344.
Cameron, L. P. & Olson, D. E. (2018). ACS Chem. Neurosci., 9, 2344-2357.
Dolomanov, 0. V., Bourhis, L. J., Gildea, R. J., Howard, J. A. K. & Puschmann, H. (2009). J. Appl. Cryst. 42, Ii-, 339-341.
Jimenez-Garrido, D. F., Gomez-Sousa, M., Ona, G., Dos Santos, R. G., Hallak, J. E. C., Alcazar-Corcoles, M. A. & Bouso, J. C. (2020). Sci. Rep. 10, 4075.
Johnson, M. W., Hendricks, P. S., Barrett, F. S. & Griffiths, R. R. (2019). Pharmaco/. Therapeut. 197, 83-102.
Sheldrick, G. M. (2015a). Acta Cryst. A71, 3-8.
Sheldrick, G. M. (2015b). Acta Cryst. C71, 3-8.
Sherwood, A. M., Halberstadt, A. L., Klein, A. K., McCorvy, J. D., Kaylo, K. W., Kargbo, R. 8. & Meisenheimer, P. (2020). J. Nat. Prod. 83, 461-467.
Shulgin, A. T. & Shulgin, A. (2016). TiKHAL: The Continuation. Isomerdesign. Available at:http://isomerdesign.com/PiHKAI/read. php?domain=tk&id=56. Accessed Mar. 19, 2020.
International Preliminary Report on Patentability in International Application No. PCT/US2021/030597, dated Nov. 17, 2022.

*Primary Examiner* — Rebecca L Anderson
(74) *Attorney, Agent, or Firm* — RAPHAEL BELLUM PLLC

(57) ABSTRACT

The disclosure relates to N-methyl-N-allyl-tryptamine (MALT) hydrofumarate, crystalline MALT hydrofumarate, N—N-dibutyl-tryptamine (DBT) iodide, crystalline DBT iodide, crystalline N-ethyl-N-propyl-tryptamine (EPT) hydrofumarate, and crystalline N—N-diisopropyl-tryptamine (DiPT) hydrofumarate, compositions containing them, and the methods of treatment using them.

8 Claims, 14 Drawing Sheets

CRYSTALLINE DIMETHYL TRYPTAMINE ANALOGUES

CROSS-REFERENCE TO RELATED APPLICATIONS

This application claims priority to U.S. Provisional Application No. 63/019,579 filed on May 4, 2020, the disclosure of which is incorporated by reference.

TECHNICAL FIELD

This disclosure relates to N,N-dimethyl-tryptamine (DMT) analogues and crystalline DMT analogues, to pharmaceutical compositions containing them and to methods of treatment/therapeutic uses of the DMT analogues and the pharmaceutical compositions. The DMT analogues are N-methyl-N-allyl-tryptamine (MALT) hydrofumarate, N—N-dibutyl-tryptamine (DBT) iodide, crystalline N-ethyl-N-propyl-tryptamine (EPT) hydrofumarate, crystalline MALT hydrofumarate, crystalline DBT iodide, and crystalline N—N-diisopropyl-tryptamine (DiPT) hydrofumarate.

BACKGROUND

Ayahuasca is the traditional spiritual medicine of the indigenous people of the Amazon basin and has a history of use in religious ceremonies dating back to the 1400s or earlier. It is an herbal tea that is made by boiling a mixture of leaves and bark. The leaves of the *Psychotria viridis* plant contain about 0.3% of N,N-di-methyl-tryptamine (DMT) by mass, which is the primary psychoactive in ayahuasca. The bark of the *Banisteriopsis coapi* vine contains many different b-carbolines; these b-carbolines function as mono-amine oxidase (MAO) inhibitors, which prevent the degradation of DMT in the human gut. Without the inhibition of mono-amine oxidase, DMT is not orally active (Cameron & Olson, 2018).

B-carboline MAO inhibitors have been identified in species of "magic mushrooms," where the primary psychedelic, psilocin, can be similarly degraded by MAO. This is the first instance of a synchronous biosynthesis of an active ingredient and the inhibitor of its degradation in a natural psychedelic species (Blei, et aL. 2020). Psilocin (4-hydroxy-N, N-di-methyl-tryptamine) is orally active in the absence of MAO inhibitors, indicating that the 4-hydroxy substitution makes the compound more resistant to deamination by MAO (Sherwood, et aL. 2020). The presence of b-carbolines in "magic mushrooms" and the varied activity of psilocin and DMT bring many questions forward on the nature of cooperative activity among chemicals in psychotropic natural products. This class of traditional psychedelics, as well as synthetic variants, have started to gain a great deal of interest as anti-depressants and anxiolytics (Johnson, et aL. 2019; Jimenez-Garrido, et aL. 2020).

Two synthetic analogues of DMT are N-ethyl-N-propyl-tryptamine (EPT) and N-methyl-N-allyl-tryptamine (MALT), both of which have very limited reports in literature (Ascic, et aL. 2012; Brandt, et aL. 2005a; Brandt, et aL. 2005b). There is a need therefore to develop N,N-dimethyl-tryptamine (DMT) analogues that allow for their development as an active pharmaceutical ingredient (an API) and for pharmaceutical compositions containing a DMT analogue. This disclosure answers such needs.

Although therapeutic efficacy is the primary concern for an active pharmaceutical ingredient (API), the salt and solid-state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

SUMMARY

The disclosure relates to four crystalline N,N-dimethyl-tryptamine (DMT) analogues, specifically crystalline N-ethyl-N-propyl-tryptamine (EPT) hydrofumarate, crystalline N-methyl-N-allyl-tryptamine (MALT) hydrofumarate, crystalline N—N-dibutyl-tryptamine (DBT) iodide, and crystalline N—N-diisopropyl-tryptamine (DiPT) hydrofumarate. N-methyl-N-allyl-tryptamine (MALT) hydrofumarate and N—N-dibutyl-tryptamine (DBT) iodide are themselves novel compounds.

The disclosure also relates to crystalline N-ethyl-N-propyl-tryptamine (EPT) hydrofumarate characterized by at least one of: a monoclinic, $P2_1$ crystal system space group at a temperature of about 297 K; unit cell dimensions $\alpha=7.4839\ (8)$ Å, b=14.1752 (14) Å, c=9.6461 (10) Å, a=90', b=110.537 (3)*, and g=90' at a temperature of about 297 K; an x-ray powder diffraction (XRPD) pattern substantially similar to FIG. 4; and an x-ray powder diffraction (XRPD) pattern having peaks at least two peaks selected from peaks 11.6, 15.9 and 21.2°2θ±0.2°2θ.

The disclosure also relates to crystalline N-methyl-N-allyl-tryptamine (MALT) hydrofumarate characterized by at least one of: an orthorhombic, $P2_12_12_1$ crystal system space group at a temperature of about 297 K; unit cell dimensions a=7.9845 (7) Å, b=8.5641 (6) Å, c=25.649 (2) Å, a=90', b=90', and g=90° at a temperature of about 297 K; an x-ray powder diffraction (XRPD) pattern substantially similar to FIG. 8; an x-ray powder diffraction (XRPD) pattern having peaks at least two peaks selected from peaks 11.6, 13.0, 13.8, 16.6 and 18.3°2θ±0.2°2θ and an x-ray powder diffraction (XRPD) pattern having peaks at least three peaks selected from peaks 11.6, 13.0, 13.8, 16.6 and 18.3°2θ±0.2°2θ.

The disclosure also relates to crystalline N—N-dibutyl-tryptamine (DBT) iodide characterized by at least one of: an orthorhombic, Pbca crystal system space group at a temperature of about 273 K; unit cell dimensions a=10.506 (2)

Å, b=14.860 (3) Å, c=24.540 (5) Å at a temperature of about 273 K; an x-ray powder diffraction (XRPD) pattern substantially similar to FIG. 11; or an XRPD having peaks at 7.2, 14.4, and 16.1°2θ±0.2°2θ.

The disclosure also relates to crystalline N—N-diisopropyl-tryptamine (DiPT) hydrofumarate characterized by at least one of: a monoclinic, $P2_{1/c}$ crystal system space group at a temperature of about 297 K; unit cell dimensions a=9.7954 (5) Å, b=13.6386 (6) Å, c=14.8273 (7) Å, β=101 (2)° at a temperature of about 297 K; an x-ray powder diffraction (XRPD) pattern substantially similar to FIG. 14; or an XRPD having peaks at 16.4, 18.4, and 19.0°2θ±0.2°2θ.

The disclosure also relates to compositions comprising a combination of, as a first component, crystalline EPT hydrofumarate, MALT hydrofumarate, crystalline MALT hydrofumarate, DBT iodide, crystalline DBT iodide, or crystalline DiPT hydrofumarate according to the disclosure and a second component selected from (a) a serotonergic drug, (b) a purified psilocybin derivative, (c) one or two purified cannabinoids, (d) a purified terpene, (e) an adrenergic drug, (f) a dopaminergic drug, (g) a purified erinacine, and (h) a purified hericenone.

The disclosure further relates to methods of preventing or treating a physical and/or psychological disorders comprising the step of administering to a subject in need thereof an effective amount of crystalline EPT hydrofumarate, MALT hydrofumarate, crystalline MALT hydrofumarate, DBT iodide, crystalline DBT iodide, crystalline MPT iodide, crystalline MiPT fumarate, or crystalline DiPT hydrofumarate according to the disclosure. In one embodiment the method comprises administering compositions (e.g., pharmaceutical compositions) containing one or more compounds selected from crystalline EPT hydrofumarate, MALT hydrofumarate, crystalline MALT hydrofumarate, DBT iodide, crystalline DBT iodide, crystalline MPT iodide, crystalline MiPT fumarate, and crystalline DiPT hydrofumarate.

The disclosure also relates to methods of preventing or treating inflammation and/or pain comprising the step of administering to a subject in need thereof an effective amount of crystalline EPT hydrofumarate, MALT hydrofumarate, crystalline MALT hydrofumarate, DBT iodide, crystalline DBT iodide, crystalline MPT iodide, crystalline MiPT fumarate, or crystalline DiPT hydrofumarate according to the disclosure. In one embodiment the method comprises administering compositions (e.g., pharmaceutical compositions) containing one or more compounds selected from crystalline EPT hydrofumarate, MALT hydrofumarate, crystalline MALT hydrofumarate, DBT iodide, crystalline DBT iodide, crystalline MPT iodide, crystalline MiPT fumarate, and crystalline DiPT hydrofumarate.

The disclosure also relates to N-methyl-N-allyl-tryptamine (MALT) hydrofumarate and N—N-dibutyl-tryptamine (DBT) iodide.

DETAILED DESCRIPTION

Figure 1:
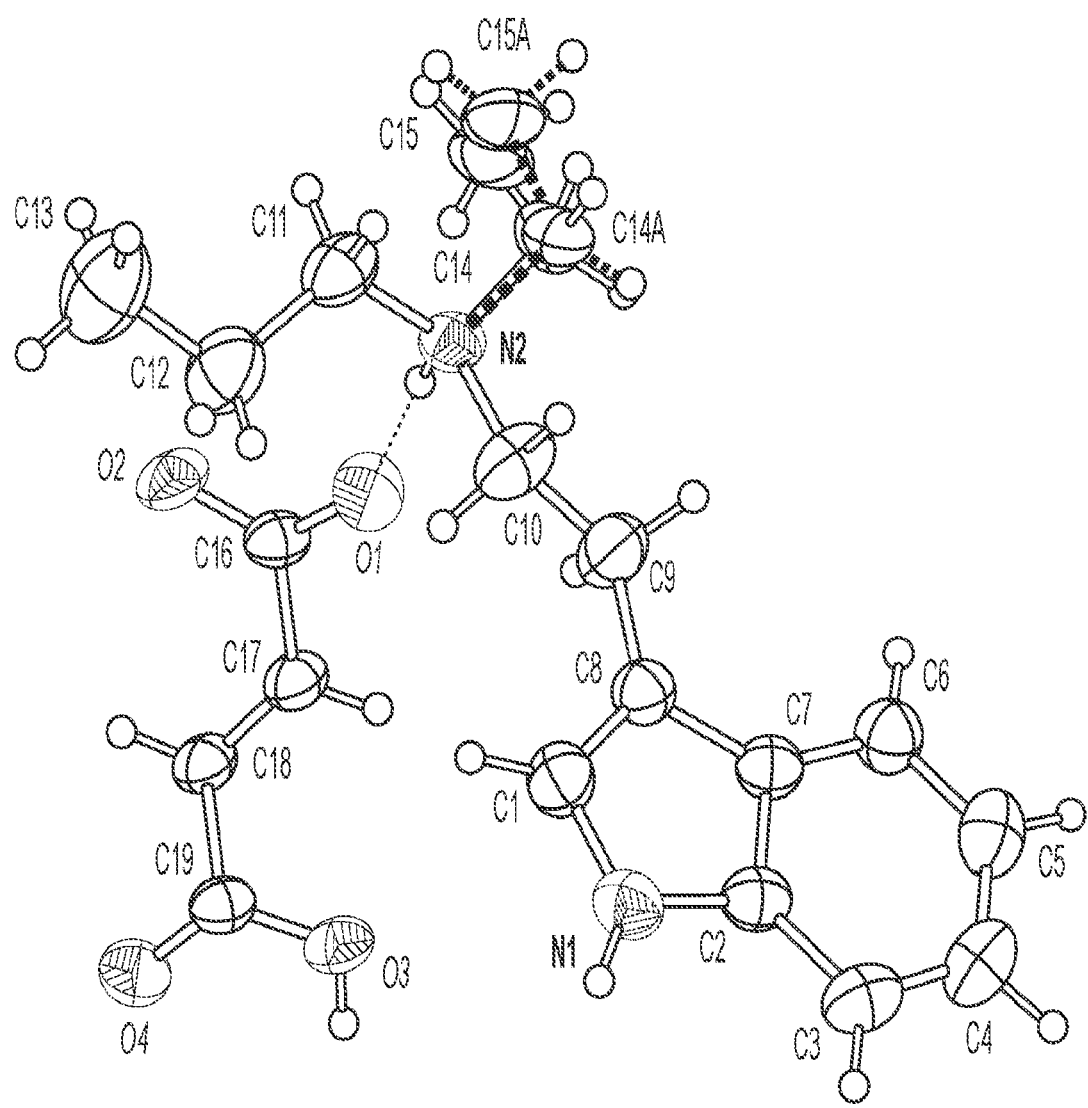
FIG. 1 depicts the molecular structure of crystalline N-ethyl-N-propyl-tryptamine (EPT) hydrofumarate with atomic labelling.

This disclosure relates DMT analogues or crystalline DMT analogues. According to the disclosure a DMT analogue or a crystalline DMT analogue includes crystalline N-ethyl-N-propyl-tryptamine (EPT) hydrofumarate, N-methyl-N-allyl-tryptamine (MALT) hydrofumarate, crystalline N-methyl-N-allyl-tryptamine (MALT) hydrofumarate, N—N-dibutyl-tryptamine (DBT) iodide, crystalline N—N-dibutyl-tryptamine (DBT) iodide, and crystalline N—N-diisopropyl-tryptamine (DiPT) hydrofumarate. This disclosure also relates to pharmaceutical compositions containing the DMT analogues or crystalline DMT analogues crystalline EPT hydrofumarate, MALT hydrofumarate, crystalline MALT hydrofumarate, DBT iodide, crystalline DBT iodide, crystalline MPT iodide, crystalline MiPT fumarate, or crystalline DiPT hydrofumarate according to the disclosure. The therapeutic uses of crystalline EPT hydrofumarate, MALT hydrofumarate, crystalline MALT hydrofumarate, DBT iodide, crystalline DBT iodide, or crystalline DiPT hydrofumarate according to the disclosure, are described below as well as compositions containing them. Crystalline EPT hydrofumarate, crystalline MALT hydrofumarate, crystalline DBT iodide, or crystalline DiPT hydrofumarate according to the disclosure, and the methods used to characterize them are described below. The novel and crystalline EPT hydrofumarate, MALT hydrofumarate, crystalline MALT hydrofumarate, DBT iodide, crystalline DBT iodide, or crystalline DiPT hydrofumarate compounds of the disclosure may be used to prepare other salts, including pharmaceutically acceptable salts, by anion exchange techniques known in the art to exchange the fumarate anion for another desired anion.

N-methyl-N-allyl-tryptamine (MALT) hydrofumarate and N—N-dibutyl-tryptamine (DBT) iodide are themselves novel compounds.

N-ethyl-N-propyl-tryptamine (EPT) hydrofumarate has the following structural formula:

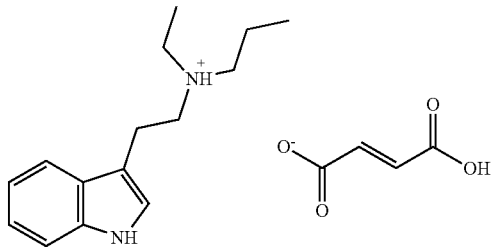 [SMILES: CCCN(CC)CCc1c[nH]c2ccccc12 ; O=C([O-])/C=C/C(=O)O]

N-methyl-N-allyl-tryptamine (MALT) hydrofumarate has the following structural formula:

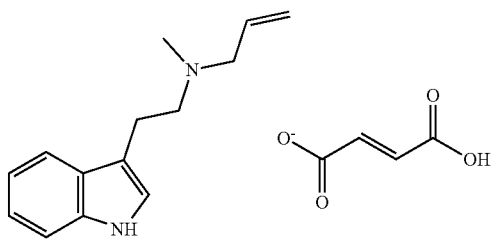 [SMILES: C=CCN(C)CCc1c[nH]c2ccccc12 ; O=C([O-])/C=C/C(=O)O]

N—N-dibutyl-tryptamine (DBT) iodide has the following structural formula:

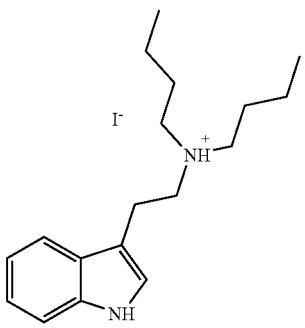 [SMILES: CCCCN(CCCC)CCc1c[nH]c2ccccc12 ; [I-]]

N—N-diisopropyl-tryptamine (DiPT) hydrofumarate has the following structural formula:

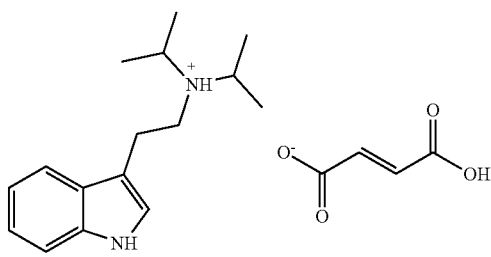 [SMILES: CC(C)N(CCc1c[nH]c2ccccc12)C(C)C ; O=C([O-])/C=C/C(=O)O]

Methods of Treatment and Therapeutic Uses

In some embodiments a DMT analogue or a crystalline DMT analogue according to the disclosure, and the methods and the compositions—particularly the pharmaceutical compositions—of the disclosure are used to regulate the activity of a neurotransmitter receptor by administering a therapeutically effective dose of a DMT analogue or a crystalline DMT analogue of the disclosure. In another embodiment, a DMT analogue or a crystalline DMT analogue according to the disclosure, and the methods and the compositions—particularly the pharmaceutical compositions—of the disclosure are used to treat inflammation and/or pain by administering a therapeutically effective dose of a DMT analogue or a crystalline DMT analogue of the disclosure.

Methods of the disclosure administer a therapeutically effective amount of a DMT analogue or a crystalline DMT analogue of the disclosure to prevent or treat a disease or condition, such as those discussed below for a subject in need of treatment. A DMT analogue or a crystalline DMT analogue of the disclosure may be administered neat or as a composition comprising a DMT analogue or a crystalline DMT analogue of the disclosure as discussed below.

A DMT analogue or a crystalline DMT analogue of the disclosure may be used to prevent and/or treat a psychological disorder. The disclosure provides a method for preventing and/or treating a psychological disorder by administering to a subject in need thereof a therapeutically effective amount of a DMT analogue or a crystalline DMT analogue of the disclosure, including the exemplary embodiments discussed herein. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

A DMT analogue or a crystalline DMT analogue of the disclosure may be used to prevent and/or treat a brain disorder. The disclosure provides a method for preventing and/or treating a brain disorder by administering to a subject in need thereof a therapeutically effective amount of a DMT analogue or a crystalline DMT analogue of the disclosure, including the exemplary embodiments discussed above. The brain disorder is chosen from Huntington's disease, Alzheimer's disease, dementia, and Parkinson's disease.

A DMT analogue or a crystalline DMT analogue of the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of a DMT analogue or a crystalline DMT analogue of the disclosure, including the exemplary embodiments discussed above.

A DMT analogue or a crystalline DMT analogue of the disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of a DMT analogue or a crystalline DMT analogue of the disclosure, including the exemplary embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e. mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

A DMT analogue or a crystalline DMT analogue of the disclosure may be used to modulate activity of a mitogen activating protein (MAP), comprising administering a composition of the invention. In one embodiment, the mitogen activating protein (MAP) comprises a MAP kinase (MAPk). MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, Janus Kinase 1 (JAK1), and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-α. In the central nervous system, p38-alpha regulates neuronal death and neurite degeneration, and it is a common target of Alzheimer's disease therapies. JAK1 influences cytokine signaling, including IL-2, IL-4, IFN-alpha/beta, IFN-γ, and IL-10, and it is implicated in brain aging. JNK3 is neuronal specific protein isoform of the JNKs. It is involved with the regulation of apoptosis. JNK3 also plays a role in modulating the response of cytokines, growth factors, and oxidative stress.

As used herein, the term "modulating activity of a mitogen activating protein" refers to changing, manipulating, and/or adjusting the activity of a mitogen activating protein. In one embodiment, modulating the activity of a MAP, such as a MAPK, can influence neural health, neurogenesis, neural growth and differentiation, and neurodegenerative diseases.

A DMT analogue or a crystalline DMT analogue of the disclosure may be used to modulate neurogenesis, comprising administering a composition of the invention. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

A DMT analogue or a crystalline DMT analogue of the disclosure may be used to modulate neurite outgrowth, comprising administering a composition of the invention. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

Compositions

The disclosure also relates to compositions comprising an effective amount of DMT analogues or crystalline DMT analogues of the disclosure, especially pharmaceutical compositions comprising a therapeutically effective amount of DMT analogues or crystalline DMT analogues of the disclosure and a pharmaceutically acceptable carrier (also known as a pharmaceutically acceptable excipient). As discussed above, DMT analogues or crystalline DMT analogues of the disclosure may be, for example, therapeutically useful to prevent and/or treat the psychological and other disorders discussed above.

A composition or a pharmaceutical composition of the disclosure may be in any form which contains DMT analogues or crystalline DMT analogues of the disclosure. The composition may be, for example, a tablet, capsule, liquid suspension, injectable, topical, or transdermal. The compositions or pharmaceutical compositions generally contain, for example, about 1% to about 99% by weight of DMT analogues or crystalline DMT analogues of the disclosure and, for example, 99% to 1% by weight of at least one suitable pharmaceutical excipient. In one embodiment, the composition may be between about 5% and about 75% by weight of DMT analogues or crystalline DMT analogues of the disclosure with the rest being at least one suitable pharmaceutical excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, DMT analogues or crystalline DMT analogues of the disclosure may be used as the "first purified psilocybin derivative" in the compositions described in US 2018/0221396 A1 and US 2019/0142851 A1. Accordingly, this disclosure provides a composition comprising as a first component: DMT analogues or crystalline DMT analogues of the disclosure; and a second component selected from (a) a serotonergic drug, (b) a purified psilocybin derivative, (c) one or two purified cannabinoids, and (d) a purified terpene; with the rest being at least one suitable pharmaceutical excipient or at least one other adjuvant, as discussed below. When used in such compositions as a first component comprising one or more of the DMT analogues or crystalline DMT analogues of the disclosure (crystalline EPT hydrofumarate, MALT hydrofumarate, crystalline MALT hydrofumarate, DBT iodide, crystalline DBT iodide, and crystalline DiPT hydrofumarate) with a second component selected from (a) a serotonergic drug, (b) a purified psilocybin derivative, (c) one or two purified cannabinoids, and (d) a purified terpene, the compositions represent particular embodiments of the invention. Compositions having a combination of EPT hydrofumarate, MALT hydrofumarate, DBT iodide, or DiPT hydrofumarate as a first component with a second component selected from(e) an adrenergic drug, (f) a dopaminergic drug, (g) a purified erinacine, and (h) a purified hericenone represent additional particular embodiments of the invention represented by the compositions having the DMT analogues or crystalline DMT analogues of the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed exemplary embodiments. Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments. Exemplary terpenes include but are not limited to the terpenes described in paragraphs [0160]-[0238] of US 2018/0221396 A1 and [0161]-[0300] US 2019/0142851 A1 as well as the disclosed exemplary embodiments.

This invention also relates to a composition or a pharmaceutical formulation that may comprise, consist essentially of, or consist of a DMT analogue or crystalline DMT analogue of the disclosure as a first component; and a second component selected from (e) an adrenergic drug, (f) a dopaminergic drug, (g) a purified erinacine, and (h) a purified hericenone; with the rest being at least one suitable pharmaceutical excipient or at least one other adjuvant, as discussed below. When used in such compositions as a first component the DMT analogues or crystalline DMT analogues of the disclosure (crystalline EPT hydrofumarate, MALT hydrofumarate, crystalline MALT hydrofumarate, DBT iodide, crystalline DBT iodide, or crystalline DiPT hydrofumarate) with a second component selected from (e) an adrenergic drug, (f) a dopaminergic drug, (g) a purified erinacine, and (h) a purified hericenone, the compositions represent particular embodiments of the invention. Compositions having a combination of EPT hydrofumarate, MALT hydrofumarate, DBT iodide, or DiPT hydrofumarate as a first component with a second component selected from (e) an adrenergic drug, (f) a dopaminergic drug, (g) a purified erinacine, and (h) a purified hericenone represent additional particular embodiments of the invention represented by the compositions having the DMT analogues or crystalline DMT analogues of the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A pharmaceutical formulation of the disclosure may comprise, consist essentially of, or consist of (a) DMT analogues or crystalline DMT analogues of the disclosure and (b) a second active compound selected from a serotonergic drug, a purified psilocybin derivative, a purified cannabinoid, or a purified terpene, an adrenergic drug, a dopaminergic drug, a purified erinacine, and a purified hericenone and (c) a pharmaceutically acceptable excipient. DMT analogues or crystalline DMT analogues of the disclosure and the second active compound are each present in a therapeutically effective amount using a purposefully engineered and unnaturally occurring molar ratios. Exemplary molar ratios of DMT analogues or crystalline DMT analogues of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference.

According to this disclosure a composition containing DMT analogues or crystalline DMT analogues as discussed above may be used in place of a "purified psilocybin derivative" in the compositions described in US 2018/0221396 A1 and US 2019/0142851 A1. Accordingly, the disclosure provides a pharmaceutical formulation comprising as a first component a DMT analogue or a crystalline DMT analogue of the disclosure and a second component selected from (a) a serotonergic drug, (b) a purified psilocybin derivative, (c) one or two purified cannabinoids, (d) a purified terpene, (e) an adrenergic drug, (f) a dopaminergic drug, (g) a purified erinacine, and (h) a purified hericenone; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Some exemplary serotonergic drugs include the following molecules: 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds See Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In a exemplary embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed exemplary embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl]dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (A8-THC), Delta-8-tetrahydrocannabinolic acid (A8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D.

In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine.J. In one embodiment, the compositions and methods disclosed herein comprise erinacine K In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of DMT analogues of the disclosure and a second compound selected from a serotonergic drug, a purified psilocybin derivative, a purified cannabinoid, a purified terpene, an adrenergic drug, a dopaminergic drug, a purified erinacine, or a purified hericenone in exemplary molar ratios are shown in Table 1.

TABLE 1

| Second Compound | Molar ratio of DMT analogues: second compound | Molar ratio of DMT analogues: second compound | Molar ratio of DMT analogues: second compound |
| --- | --- | --- | --- |
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |

TABLE 1-continued

| Second Compound | Molar ratio of DMT analogues: second compound | Molar ratio of DMT analogues: second compound | Molar ratio of DMT analogues: second compound |
| --- | --- | --- | --- |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |

Exemplary pharmaceutical compositions of DMT analogues of the disclosure and a second compound selected from a serotonergic drug, a purified psilocybin derivative, a purified cannabinoid, or a purified terpene and an excipient with exemplary molar ratios of DMT analogues of the disclosure to the second compound are shown in Table 2.

TABLE 2

| Second Compound | Molar ratio DMT analogues: second compound | Molar ratio of DMT analogues: second compound | Molar ratio of DMT analogues: second compound |
| --- | --- | --- | --- |
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |

TABLE 2-continued

| Second Compound | Molar ratio DMT analogues: second compound | Molar ratio of DMT analogues: second compound | Molar ratio of DMT analogues: second compound |
|---|---|---|---|
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |

An "effective amount" or a "therapeutically effective amount" of DMT analogues or crystalline DMT analogues according to the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L Limbird, eds., McGraw-Hill Press, 155-173 (2001), which is incorporated herein by reference. DMT analogues or crystalline DMT analogues according to the disclosure, compositions and pharmaceutical compositions containing them may be used in combination with other agents that are generally administered to a patient being treated for psychological and other disorders discussed above. They may also be co-formulated with one or more of such agents in a single pharmaceutical composition.

Depending on the type of composition or pharmaceutical composition, the excipient or pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter DMT analogues or crystalline DMT analogues of the disclosure or produce undesirable biological effects or otherwise interact in a deleterious manner with any other component(s) of the pharmaceutical composition.

The compositions or pharmaceutical compositions of the disclosure may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, DMT analogues or crystalline DMT analogues of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a composition or a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of DMT analogues or crystalline DMT analogues of the disclosure in pure form, with a permeation enhancer, with stabilizers (e.g., antioxidants), or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, liquid dosage forms, such as, for example, tablets, suppositories, pills, soft elastic and hard gelatin capsules, powders, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

Example 1: Crystalline N-ethyl-N-propyl-tryptammonium hydrofumarate

Preparation: Single crystals of N-ethyl-N-propyl-tryptammonium (EPT) hydrofumarate suitable for X-ray analysis were obtained from the slow evaporation of an aqueous solution of a commercial sample of EPT fumarate (The Indole Shop, Canada).

Single Crystal Characterization: Crystal data, data collection and structure refinement details for crystalline N-ethyl-N-propyl-tryptammonium (EPT) hydrofumarate are summarized in Table 3.

TABLE 3

| | EPT hydrofumarate |
|---|---|
| Chemical formula | $C_4H_3O_4 \cdot C_{15}H_{23}N_2$ |
| $M_r$ | 346.42 |
| Crystal system, space group | Monoclinic, $P2_1$ |
| Temperature (K) | 297 |
| a, b, c (Å) | 7.4839 (8), 14.1752 (14), 9.6461 (10) |
| $\alpha, \beta, \gamma$ (°) | 90, 110.537 (3), 90 |
| V (Å$^3$) | 958.28 (17) |
| Z | 2 |
| Radiation type | Mo K$\alpha$ |
| $\mu$ (mm$^{-1}$) | 0.08 |
| Crystal size (mm) | 0.42 × 0.2 × 0.1 |
| Diffractometer | Bruker D8 Venture CMOS |
| Absorption correction | Multi-scan SADABS2016/2 (Bruker, 2016 February) was used for absorption correction. wR2(int) was 0.0636 before and 0.0481 after correction. The Ratio of minimum to maximum transmission is 0.9438. The $\lambda/2$ correction factor is not present. |
| $T_{min}, T_{max}$ | 0.703, 0.745 |

TABLE 3-continued

| | EPT hydrofumarate |
|---|---|
| No. of measured, independent and observed [I > 2σ(I)] reflections | 21982, 3570, 3368 |
| $R_{int}$ | 0.028 |
| $(\sin q/l)_{max}$ (Å$^{-1}$) | 0.611 |
| $R[F^2 > 2\sigma(F^2)]$, $wR(F^2)$, S | 0.034, 0.093, 1.03 |
| No. of reflections | 3570 |
| No. of parameters | 261 |
| No. of restraints | 7 |
| H-atom treatment | H atoms treated by a mixture of independent and constrained refinement |
| $\Delta\rangle_{max}$, $\Delta\rangle_{min}$ (e Å$^{-3}$) | 0.13, −0.13 |
| Absolute structure | Flack x determined using 1509 quotients [(I+) − (I−)]/[(I+) + (I−)] (Parsons, Flack and Wagner, Acta Cryst. B69 (2013) 249-259). |
| Absolute structure parameter | 0.1 (2) |

Computer programs: OLEX3 (Bruker, 2018), APEX3 (Bruker, 2018), SAINT (Bruker, 2018), SHELXT2014 (Sheldrick, 2015a), SHELXL2018 (Sheldrick, 2015b), OLEX2 (Dolomanov et al., 2009), publCIF (Westrip, 2010).

Figure 2:
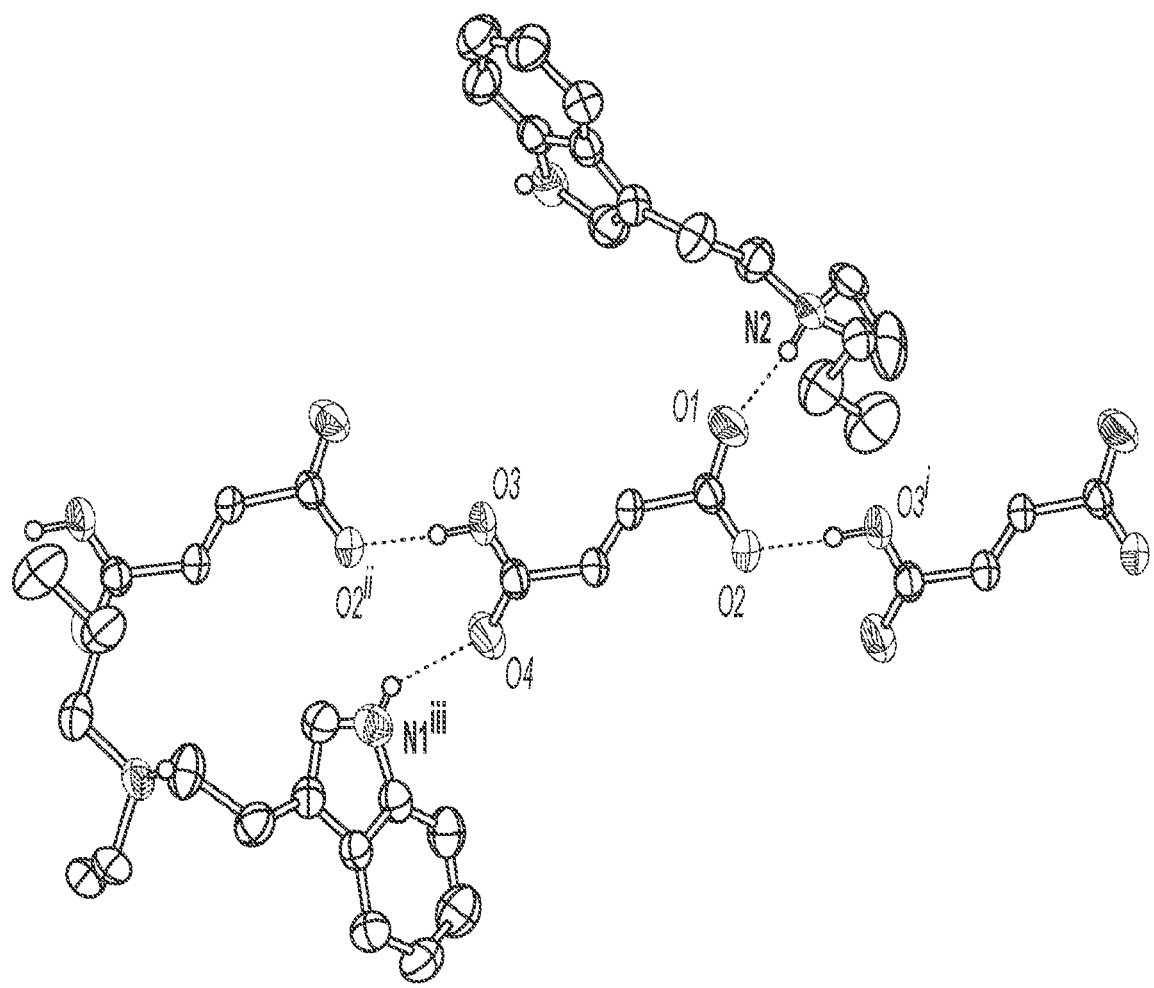
FIG. 2 shows the hydrogen bonding of a hydrofumarate ion in the structure of crystalline N-ethyl-N-propyl-tryptammonium (EPT) hydrofumarate, with hydrogen bonds shown as dashed lines.
Figure 3:
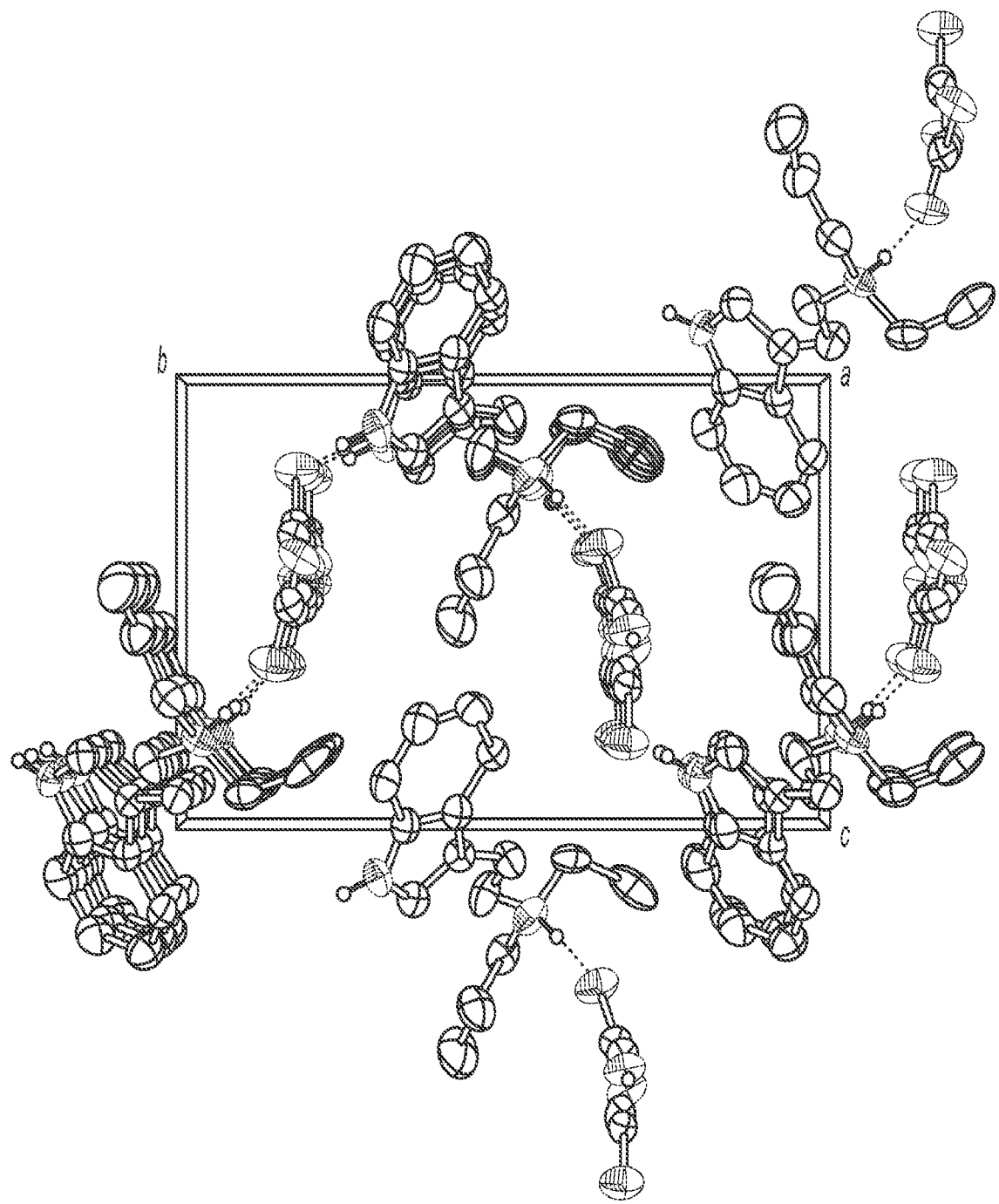
FIG. 3 shows the unit cell of crystalline N-ethyl-N-propyl-tryptammonium (EPT) hydrofumarate.

The molecular structure of crystalline N-ethyl-N-propyl-tryptammonium (EPT) hydrofumarate showing the atom labelling is shown in FIG. 1. Displacement ellipsoids are drawn at the 50% probability level. Dashed bonds indicate the disordered component of the structure. Hydrogen bonds are shown as dashed lines. In FIG. 1 only one component of the disorder is shown. FIG. 2 shows the hydrogen bonding of a hydrofumarate ion in the structure of crystalline N-ethyl-N-propyltryptammonium hydrofumarate, with hydrogen bonds shown as dashed lines. Displacement ellipsoids are drawn at the 50% probability level. Only one component of the disorder is shown, and hydrogen atoms not involved in hydrogen bonding are omitted for clarity. Symmetry codes: (i) −1+x, y, z; (ii) 1+x, y, z; (iii) 2−x, −1/2+y, 1−z. FIG. 3 shows the unit cell of crystalline N-ethyl-N-propyl-tryptammonium (EPT) hydrofumarate. The crystal packing of crystalline EPT hydrofumarate is shown along the a axis. The hydrogen bonds are shown as dashed lines. Displacement ellipsoids are drawn at the 50% probability level. Hydrogen atoms not involved in hydrogen bonding are omitted for clarity. In FIG. 1 only one component of the disorder is shown.

The tryptammonium cations and the hydrofumarate anions of the EPT salt are held together in infinite two-dimensional networks parallel to (001) through N—H. . . O and O—H. . . O hydrogen bonds. The indole N—H hydrogen bonds to the carbonyl oxygen of the carboxylic acid of a hydrofumarate molecule. The ammonium N—H and the carboxylic acid O—H each hydrogen bond to one of the carboxylate oxygens (FIG. 2). The packing of N-ethyl-N-propyl-tryptammonium hydrofumarate is shown in FIG. 3.

Simulated Powder X-ray Diffraction (PXRD) Pattern

Figure 4:
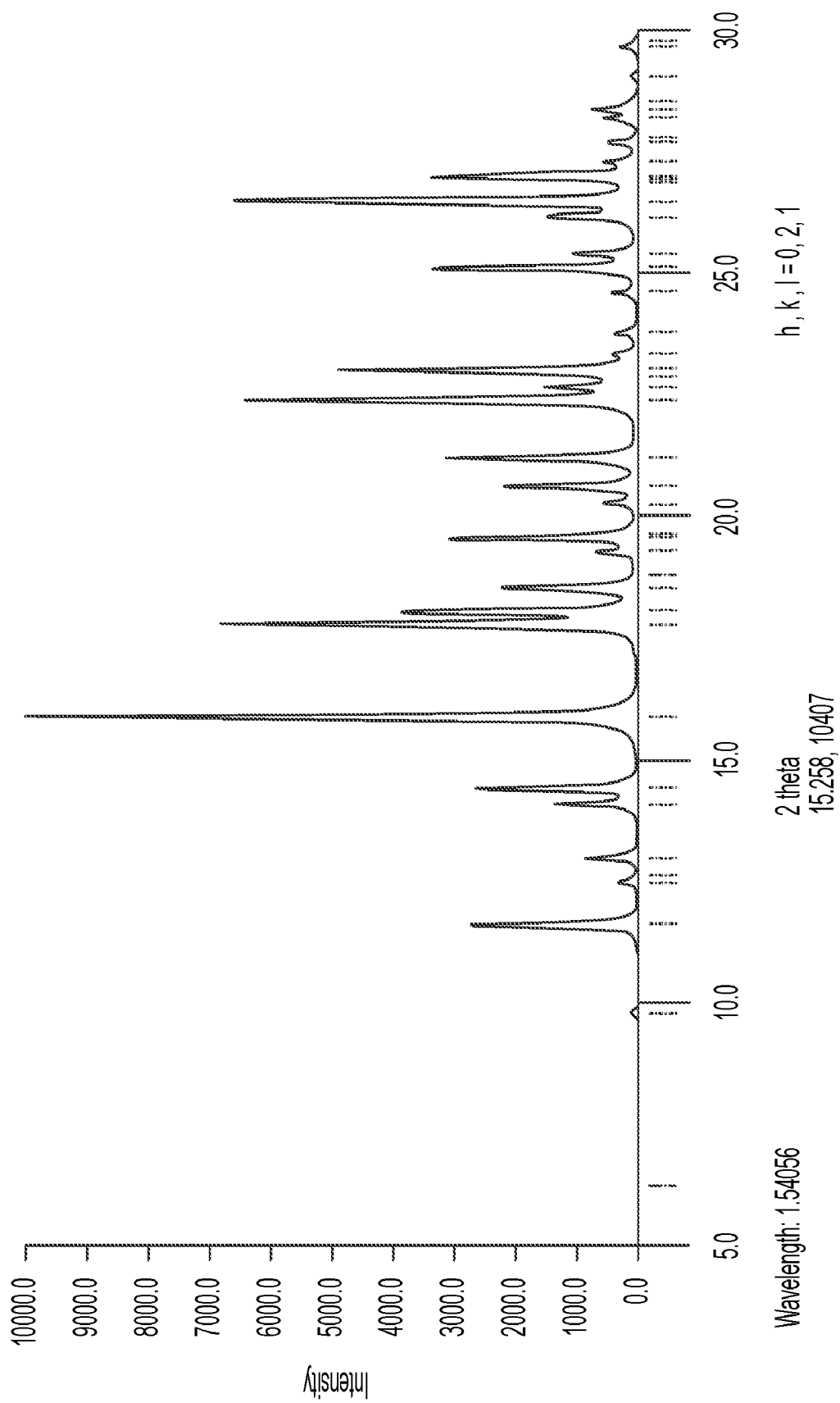
FIG. 4 depicts a simulated X-ray powder diffraction (XRPD) pattern for crystalline N-ethyl-N-propyl-tryptammonium (EPT) hydrofumarate generated from its single crystal data.

FIG. 4 is a simulated X-ray powder diffraction (XRPD) pattern for crystalline N-ethyl-N-propyl-tryptammonium (EPT) hydrofumarate generated from its single crystal data. Table 4 lists the angles, °2θ±0.2° 2θ, and d-spacing of the peaks identified in the experimental XRPD pattern of FIG. 4. The entire list of peaks, or a subset thereof, may be sufficient to characterize the cocrystal. For example, the cocrystal may be characterized by at least two peaks selected from the peaks at 11.6, 15.9 and 21.2°2θ±0.2°2θ as well as by a XRPD pattern substantially similar to FIG. 4.

TABLE 4

| d-spacing | 2 Theta(deg) | Intensity |
|---|---|---|
| 9.03 | 9.8 | 94. |
| 7.62 | 11.6 | 2669.844 |
| 7.09 | 12.5 | 326.826 |
| 7.01 | 12.6 | 16.20246 |
| 6.81 | 13.0 | 1006.218 |
| 6.28 | 14.1 | 1839.756 |
| 6.14 | 14.4 | 4075.2 |
| 5.58 | 15.9 | 18046.36 |
| 4.98 | 17.8 | 15375.6 |
| 4.91 | 18.0 | 8620.68 |
| 4.78 | 18.5 | 5651 |
| 4.60 | 19.3 | 1696.468 |
| 4.53 | 19.6 | 8778.84 |
| 4.52 | 19.6 | 254.764 |
| 4.38 | 20.3 | 1580.768 |
| 4.30 | 20.6 | 6799.28 |
| 4.19 | 21.2 | 10155.4 |
| 3.97 | 22.4 | 23493.64 |
| 3.91 | 22.7 | 4862.12 |
| 3.88 | 22.9 | 1817.312 |
| 3.86 | 23.0 | 18618.52 |
| 3.81 | 23.3 | 1087.736 |
| 3.74 | 23.8 | 1622.89 |
| 3.62 | 24.6 | 1833.88 |
| 3.54 | 25.1 | 16106.72 |
| 3.50 | 25.4 | 4534.8 |
| 3.41 | 26.1 | 556.98 |
| 3.40 | 26.2 | 6586.28 |
| 3.36 | 26.5 | 34905 |
| 3.31 | 26.9 | 721.24 |
| 3.31 | 26.9 | 573.22 |
| 3.31 | 27.0 | 45.3734 |
| 3.30 | 27.0 | 17353.64 |
| 3.30 | 27.0 | 540.872 |
| 3.26 | 27.3 | 2692.924 |
| 3.22 | 27.7 | 2637.988 |
| 3.20 | 27.8 | 2.07452 |
| 3.16 | 28.2 | 3142.324 |
| 3.14 | 28.4 | 835.204 |
| 3.14 | 28.4 | 3552.696 |
| 3.13 | 28.5 | 543.024 |
| 3.07 | 29.1 | 846.596 |
| 3.01 | 29.6 | 2255.5 |
| 3.00 | 29.8 | 287.1924 |

Example 2: N-methyl-N-allyl-tryptammonium (MALT) hydrofumarate and crystalline MALT hydrofumarate Preparation: 134 mg of a commercial sample of N-methyl-N-allyl-tryptamine (The Indole Shop, Canada), which is a waxy solid that does not crystallize well, was dissolved in 10 mL of methanol, and 68 mg of fumaric acid was added. The mixture was refluxed for 12 hours and solvent was removed in vacuo to obtain a waxy, yellow product. The material was recrystallized from ethanol to yield colorless single crystals suitable for X-ray diffraction. The product was also characterized by nuclear magnetic resonance. $^1$H NMR (400 MHz, D$_2$O): d 7.69 (d, J=7.9 Hz, 1H, ArH), 7.34 (s, 1H, ArH), 7.29 (t, J=7.1 Hz, 1 H, ArH), 7.21 (t, J=7.1 Hz, 1H, ArH), 6.66 (s, 2H, CH), 6.92-5.82 (m, 1H, CH), 5.60-5.56 (m, 2H, CH$_2$), 3.88-3.83 (m, 1H, CH$_2$), 3.77-3.72 (m, 1H, CH$_2$), 3.68-3.57 (m, 1H, CH$_2$), 3.44-3.37 (m, 1H, CH$_2$), 3.34-3.21 (m, 2H, CH$_2$), 2.90 (s, 3H, CH$_3$). $^{13}$C NMR (100 MHz, D$_2$O): d 172.2 (COOH), 137.0 (CH), 135.5 (ArC), 127.3 (ArC), 126.9 (ArC), 126.2 (ArC), 124.8 (ArC), 122.9 (ArC), 120.1 (ArC), 118.9 (ArC), 112.7 (sp$^2$q, 109.0 (sp$^2$C), 58.7 (AkC), 55.6 (AkC), 40.1 (AkC), 20.6 (AkC).

Figure 7:
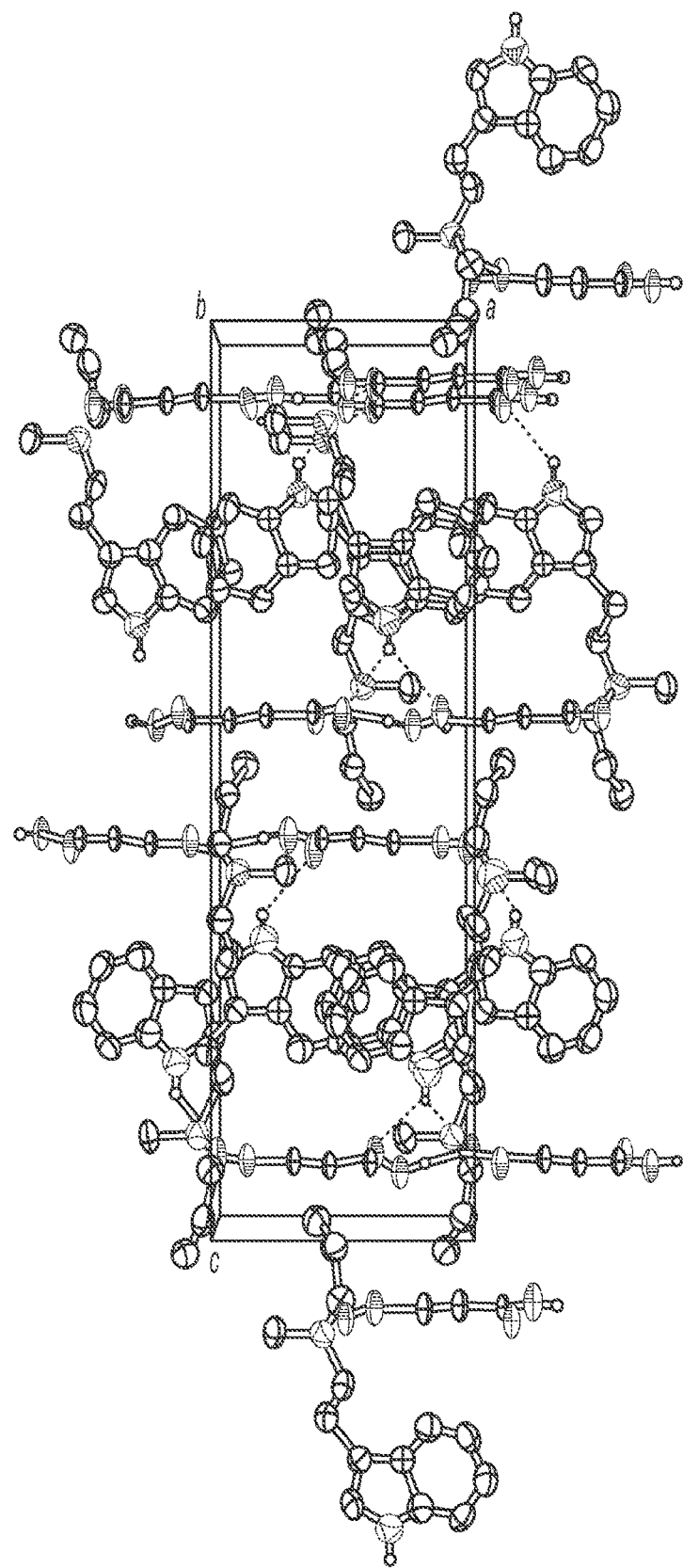
FIG. 7 shows the unit cell of crystalline N-methyl-N-allyl-tryptammonium (MALT) hydrofumarate.

Single Crystal Characterization: Crystal data, data collection and structure refinement details are summarized in Table 5.

ability level. Hydrogen atoms not involved in hydrogen bonding are omitted for clarity. Symmetry codes: (i) 1+x, y, z; (ii) 1−x, 1/2+y, 1/2−z; (iii) −1+x, y, z; (iv) −x, 1/2+y, 1/2−z. FIG. 7 shows the crystal packing of MALT hydrofumarate shown along the b axis. The hydrogen bonds are shown as dashed lines. Displacement ellipsoids are drawn at the 50% probability level. Hydrogen atoms not involved in hydrogen bonding are omitted for clarity. The unit cell of N-methyl-N-allyl-tryptammonium hydrofumarate contains one tryptammonium cation and one hydrofumarate anion (FIG. 7). The tryptammonium has a near planar indole, with a mean deviation from planarity of 0.007 Å. The ethylamino group is turned away from the plane of the indole, with a C1-C8-C9-C10 torsion angle of −105.5 (5). The hydrofumarate is also near planar, with a r.m.s. deviation of 0.055 Å. The carboxylate is partially delocalized, with C—O distances of 1.239 (5) A and 1.259 (4) A.

The tryptammonium cations and the hydro-fumarate anions of the MALT salt are held together in infinite two-dimensional networks parallel to (001) through N—H. . . O and O—H. . . O hydrogen bonds. The ammonium N—H

TABLE 5

| | MALT Hydrofumarate |
|---|---|
| Chemical formula | C$_4$H$_3$O$_4$•C$_{14}$H$_{19}$N$_2$ |
| M$_r$ | 330.37 |
| Crystal system, space group | Orthorhombic, P2$_1$2$_1$2$_1$ |
| Temperature (K) | 297 |
| a, b, c (Å) | 7.9845 (7), 8.5641 (6), 25.649 (2) |
| α, β, γ (°) | 90, 90, 90 |
| V (Å$^3$) | 1753.9 (3) |
| Z | 4 |
| Radiation type | Mo Kα |
| μ (mm$^{-1}$) | 0.09 |
| Crystal size (mm) | 0.42 × 0.24 × 0.15 |
| Diffractometer | Bruker D8 Venture CMOS |
| Absorption correction | Multi-scan |
| | SADABS2016/2 (Bruker, 2016 February) was used for absorption correction. wR2(int) was 0.0704 before and 0.0622 after correction. The Ratio of minimum to maximum transmission is 0.9131. The λ/2 correction factor is not present. |
| T$_{min}$, T$_{max}$ | 0.681, 0.745 |
| No. of measured, independent and observed [I > 2σ(I)] reflections | 49712, 3318, 3036 |
| R$_{int}$ | 0.046 |
| (sin q/l)$_{max}$ (Å$^{-1}$) | 0.610 |
| R[F$^2$ > 2σ(F$^2$)], wR(F$^2$), S | 0.053, 0.147, 1.10 |
| No. of reflections | 3318 |
| No. of parameters | 228 |
| No. of restraints | 4 |
| H-atom treatment | H atoms treated by a mixture of independent and constrained refinement |
| Δ⟩$_{max}$, Δ⟩$_{min}$ (e Å$^{-3}$) | 0.25, −0.17 |
| Absolute structure | Flack x determined using 1177 quotients [(I+) − (I−)]/[(I+) + (I−)] (Parsons, Flack and Wagner, Acta Cryst. B69 (2013) 249-259). |
| Absolute structure parameter | 0.0 (3) |

Computer programs: OLEX3 (Bruker, 2018), APEX3 (Bruker, 2018), SAINT (Bruker, 2018), SHELXT2014 (Sheldrick, 2015a), SHELXL2018 (Sheldrick, 2015b), OLEX2 (Dolomanov et al., 2009), pubICIF (Westrip, 2010).

Figure 5:
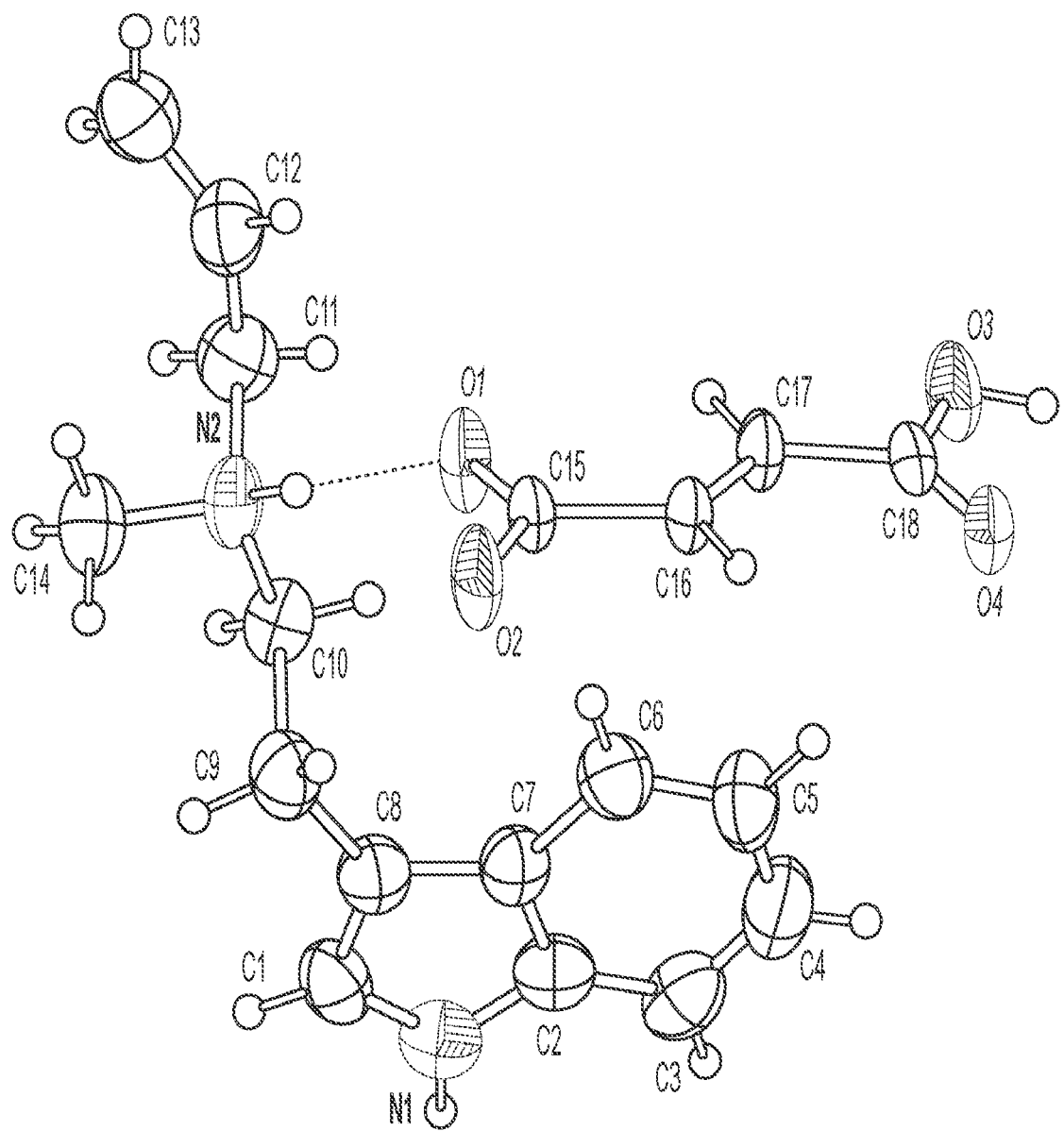
FIG. 5 depicts the molecular structure of crystalline N-methyl-N-allyl-tryptamine (MALT) hydrofumarate with atomic labelling.
Figure 6:
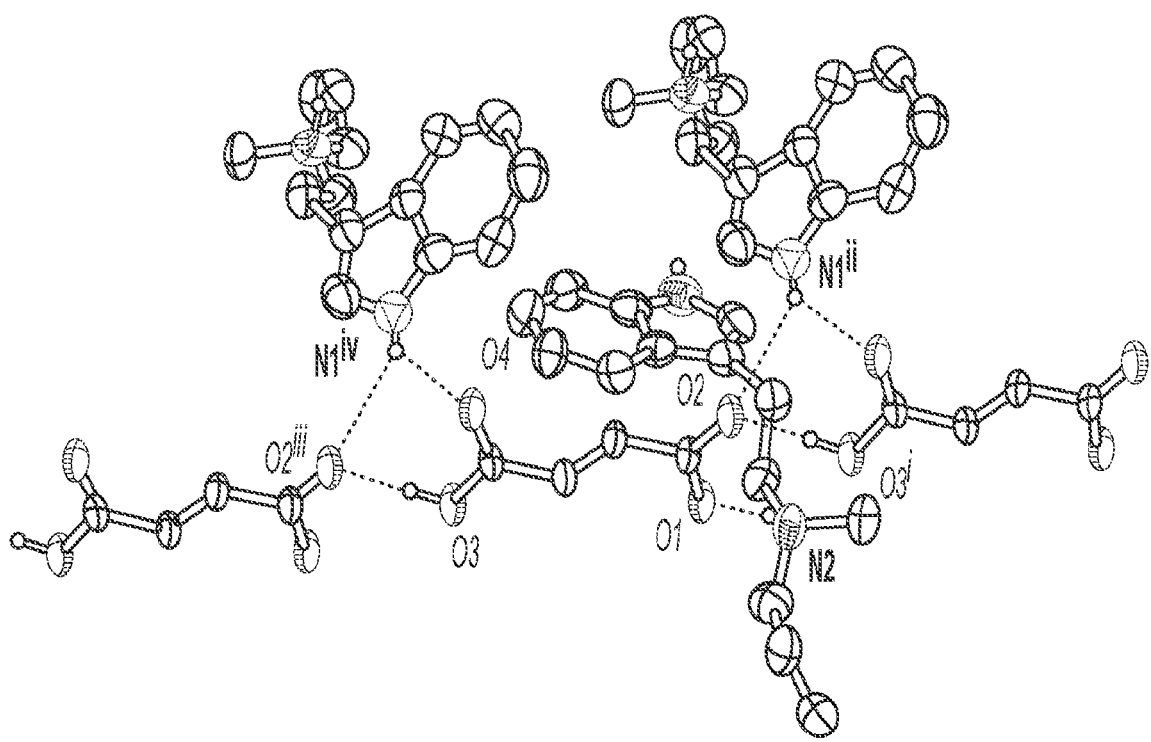
FIG. 6 shows the hydrogen bonding of a hydrofumarate ion in the structure of crystalline N-methyl-N-allyl-tryptamine (MALT) hydrofumarate, with hydrogen bonds shown as dashed lines.

The molecular structure of N-methyl-N-allyltryptammonium hydrofumarate showing the atom labelling is shown in FIG. 5. Displacement ellipsoids are drawn at the 50% probability level. Hydrogen bonds are shown as dashed lines. FIG. 4 shows the hydrogen bonding of a hydrofumarate ion in the structure of N-methyl-N-allyltryptammonium hydrofumarate, with hydrogen bonds shown as dashed lines. Displacement ellipsoids are drawn at the 50% probability level. Hydrogen atoms not involved in hydrogen bonding are omitted for clarity. The indole N—H has a three-centre (bifurcated) hydrogen bond with the carbonyl oxygen of a carboxylic acid of a hydrofumarate anion, and a carboxyl-ate oxygen of a different hydrofumarate anion. The carb-oxy-lic acid O—H hydrogen bonds to a carboxyl-ate oxygen of another hydrofumarate anion. The packing of the N-methyl-N-allyl-tryptammonium hydrofumarate is shown in FIG. 7.

Figure 8:
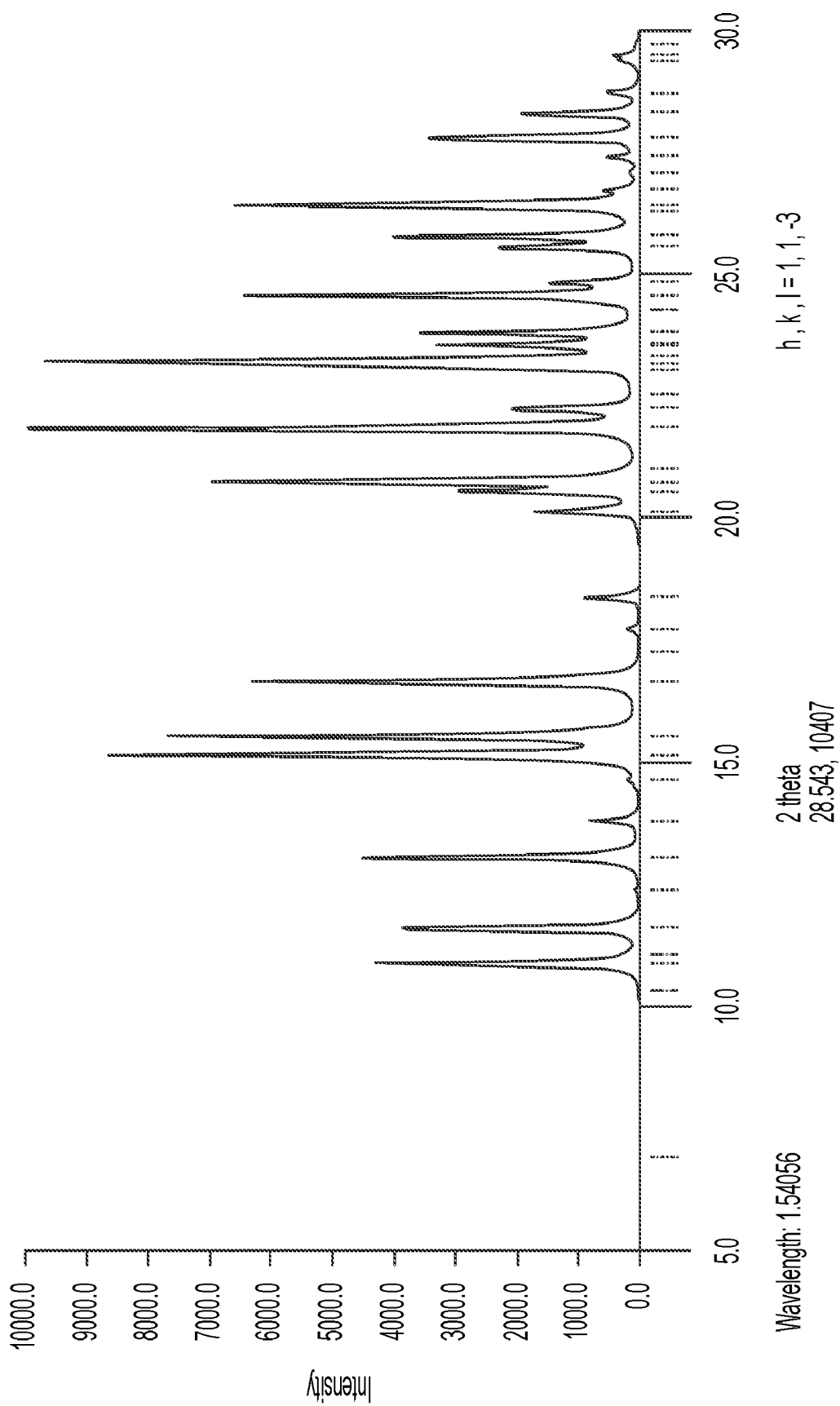
FIG. 8 depicts a simulated X-ray powder diffraction (XRPD) pattern for crystalline N-methyl-N-allyl-tryptammonium (MALT) hydrofumarate generated from its single crystal data.
Figure 9:
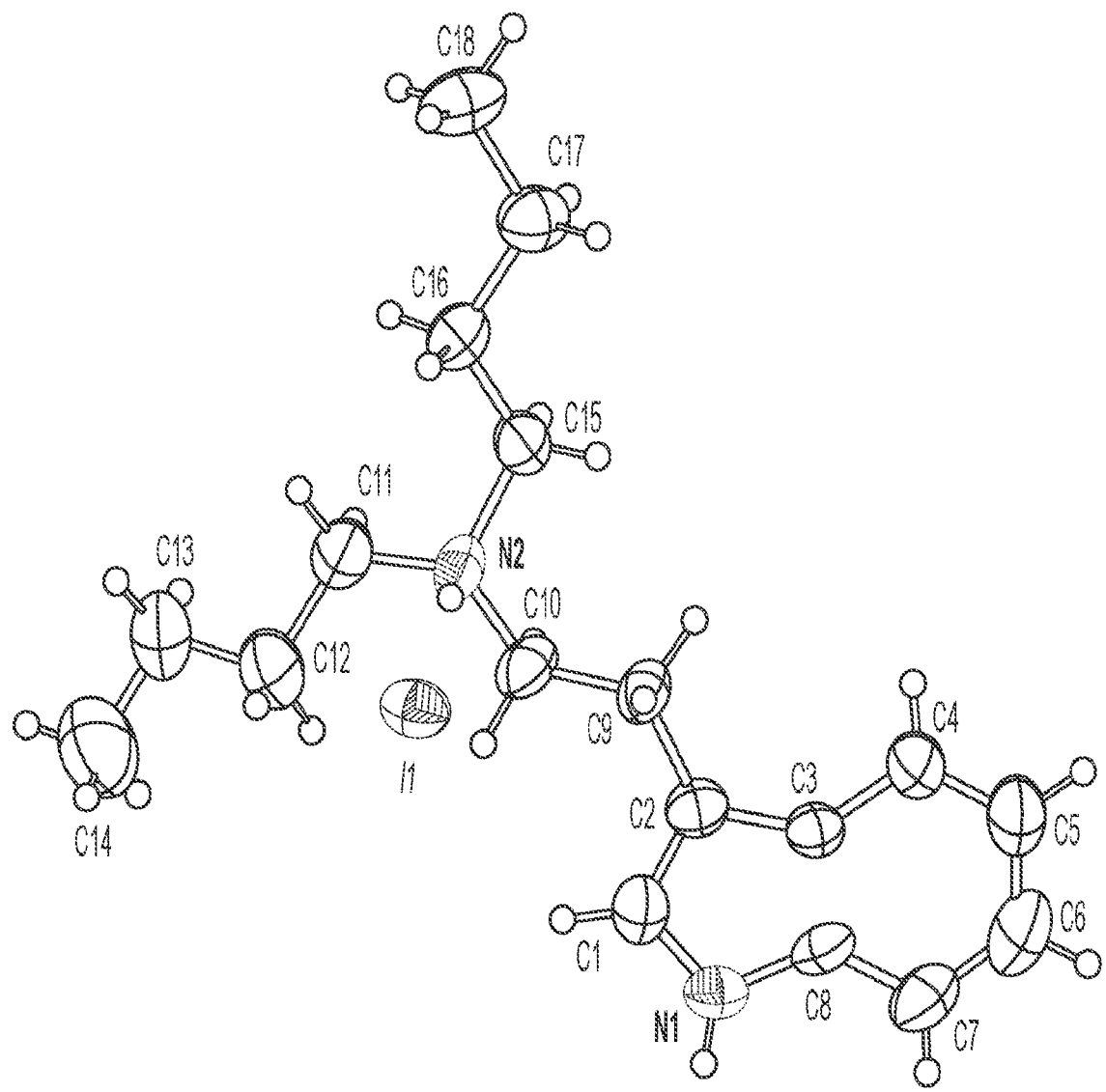
FIG. 9 depicts the molecular structure of crystalline N—N-dibutyl-tryptamine (DBT) iodide with atomic labelling.
Figure 10:
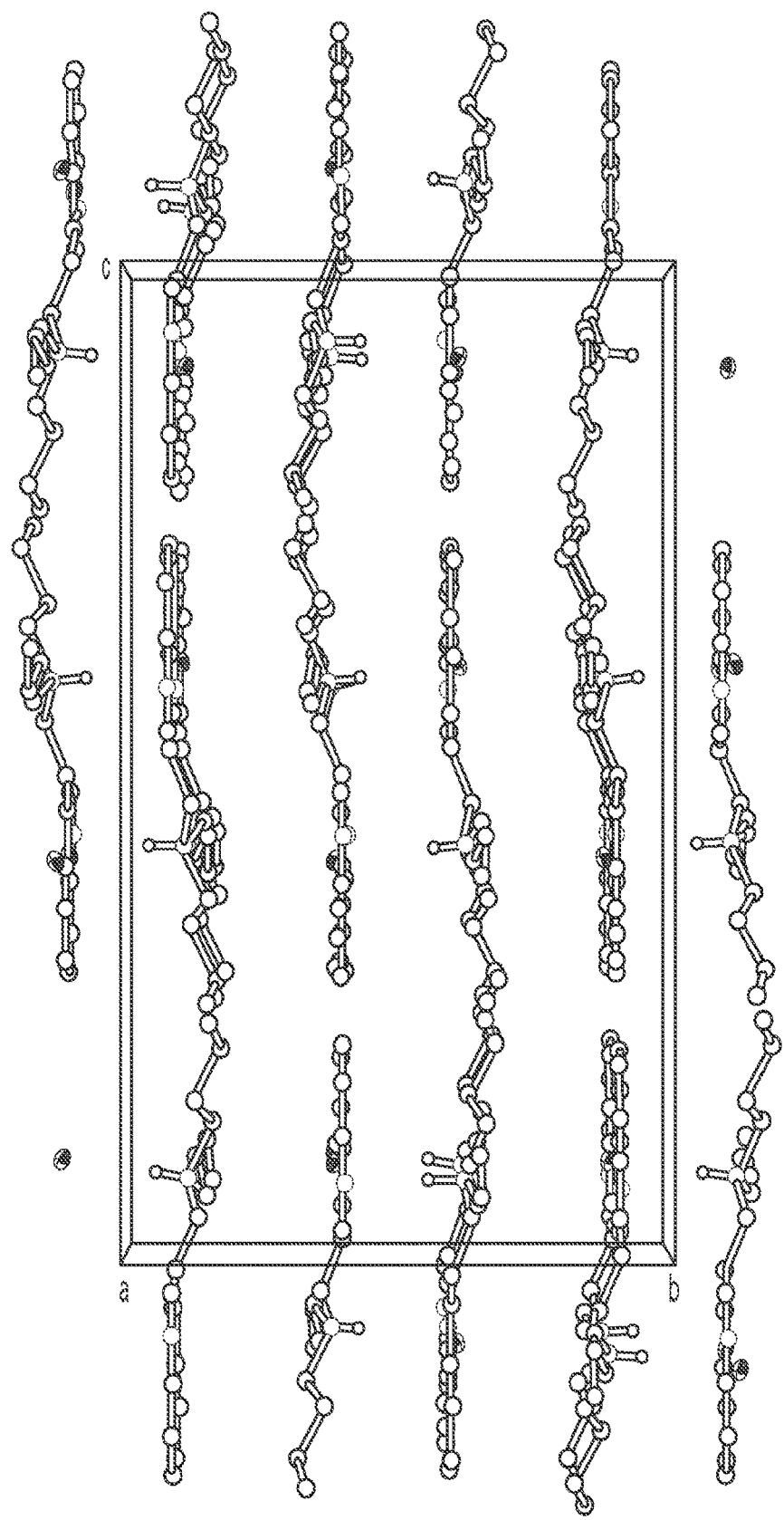
FIG. 10 shows the unit cell of crystalline N—N-dibutyl-tryptamine (DBT) iodide.

Simulated Powder X-ray Diffraction (PXRD) Pattern: FIG. 8 is a simulated X-ray powder diffraction (XRPD) pattern for crystalline N-ethyl-N-propyl-tryptammonium (EPT) hydrofumarate generated from its single crystal data. Table 6 lists the angles, °2θ±0.2°2θ, and d-spacing of the peaks identified in the experimental XRPD pattern of FIG. 8. The entire list of peaks, or a subset thereof, may be sufficient to characterize the cocrystal. For example, the cocrystal may be characterized by at least two or at least three peaks selected from the peaks at 11.6, 13.0, 13.8, 16.6 and 18.3°2θ±0.2°2θ as well as by a XRPD pattern substantially similar to FIG. 8.

TABLE 6

| d-spacing | 2 Theta(deg) | Intensity |
|---|---|---|
| 12.82 | 6.9 | 0.242868 |
| 8.12 | 10.9 | 8574.84 |
| 7.62 | 11.6 | 8656.48 |
| 7.12 | 12.4 | 70.4676 |
| 6.78 | 13.0 | 13427.56 |
| 6.41 | 13.8 | 2507.64 |
| 6.05 | 14.6 | 387.204 |
| 5.84 | 15.1 | 24206.64 |
| 5.84 | 15.1 | 9471.48 |
| 5.69 | 15.5 | 31756.32 |
| 5.31 | 16.6 | 30182.8 |
| 5.13 | 17.2 | 1.181308 |
| 5.00 | 17.7 | 1084.852 |
| 4.82 | 18.3 | 5484.664 |
| 4.40 | 20.1 | 11304.48 |
| 4.32 | 20.4 | 17683.92 |
| 4.32 | 20.5 | 1595.1 |
| 4.28 | 20.6 | 801.546 |
| 4.27 | 20.6 | 49909.4 |
| 4.22 | 20.9 | 585.54 |
| 4.06 | 21.7 | 82909.2 |
| 3.99 | 22.1 | 17132.88 |
| 3.94 | 22.4 | 321.7512 |
| 3.85 | 22.9 | 2544.728 |
| 3.83 | 23.1 | 85018.4 |
| 3.82 | 23.1 | 6811.84 |
| 3.81 | 23.2 | 473.64 |
| 3.77 | 23.4 | 28270.92 |
| 3.77 | 23.4 | 896.22 |
| 3.73 | 23.6 | 34492.32 |

TABLE 6-continued

| d-spacing | 2 Theta(deg) | Intensity |
|---|---|---|
| 3.62 | 24.4 | 52610.8 |
| 3.62 | 24.4 | 13947.52 |
| 3.62 | 24.4 | 2417.728 |
| 3.58 | 24.6 | 13977.92 |
| 3.56 | 24.8 | 81.6276 |
| 3.48 | 25.3 | 24432.4 |
| 3.45 | 25.6 | 46305.6 |
| 3.45 | 25.6 | 62.19336 |
| 3.39 | 26.0 | 3119.16 |
| 3.37 | 26.2 | 81174.4 |
| 3.33 | 26.5 | 5491.92 |
| 3.33 | 26.5 | 132.2176 |
| 3.29 | 26.9 | 1413.888 |
| 3.25 | 27.1 | 6170.456 |
| 3.21 | 27.5 | 47700.4 |
| 3.15 | 28.0 | 3461.2 |
| 3.15 | 28.0 | 24178.96 |
| 3.10 | 28.4 | 8100.96 |
| 3.04 | 29.0 | 5070.024 |
| 3.03 | 29.2 | 6579.72 |
| 3.00 | 29.4 | 907.988 |

Example 3: N—N-dibutyl-tryptamine (DBT) iodide and crystalline DBT iodide

Preparation: 208 mg of tryptamine was dissolved in 10 mL of THF and 1.50 mL of 1-Iodobutane. The mixture was refluxed under nitrogen for 5 days. The solvent was removed in vacuo to yield a brown oil. The oil was recrystallized from acetone to yield colorless crystalline solid. Crystals suitable for X-ray diffraction were obtained from slow evaporation of an ethanol solution. The product was also characterized by nuclear magnetic resonance. $^1$H NMR (400 MHz, $D_2O$) δ 7.70 (d, J=8.0 Hz, 1H, ArH), 7.55 (d, J=7.6 Hz, 1H, ArH), 7.34-7.28 (m, 2H, ArH), 7.22 (t, J=8.0 Hz, 1H, ArH), 3.53 (t, J=7.3 Hz, 2H, $CH_2$), 3.29-3.18 (m, 6H, $CH_2$), 1.69-1.61 (m, 4H, $CH_2$), 1.36-1.31 (m, 4H, $CH_2$), 0.90 (t, J=7.4 Hz, 6H, $CH_3$).

Single Crystal Characterization: Crystal data, data collection and structure refinement details are summarized in Table 7.

TABLE 7

| | DBT iodide |
|---|---|
| Chemical formula | I·$C_{18}H_{29}N_2$ |
| $M_r$ | 400.33 |
| Crystal system, space group | Orthorhombic, Pbca |
| Temperature (K) | 273 |
| a, b, c (Å) | 10.506 (2), 14.860 (3), 24.540 (5) |
| V (Å$^3$) | 3831.0 (13) |
| Z | 8 |
| Radiation type | Mo Kα |
| μ (mm$^{-1}$) | 1.67 |
| Crystal size (mm) | 0.25 × 0.1 × 0.02 |
| Diffractometer | Bruker APEX-II CCD |
| Absorption correction | Multi-scan |
| | SADABS2016/2 (Bruker, 2016 February) was used for absorption correction. wR2(int) was 0.0617 before and 0.0540 after correction. The Ratio of minimum to maximum transmission is 0.9173. The λ/2 correction factor is Not present. |
| $T_{min}$, $T_{max}$ | 0.684, 0.745 |
| No. of measured, independent and observed [I > 2σ(I)] reflections | 49317, 3510, 2546 |

TABLE 7-continued

| | DBT iodide |
|---|---|
| $R_{int}$ | 0.090 |
| $R[F^2 > 2\sigma(F^2)]$, $WR(F^2)$, S | 0.046, 0.070, 1.13 |
| No. of reflections | 3510 |
| No. of parameters | 218 |
| No. of restraints | 26 |
| H-atom treatment | H atoms treated by a mixture of independent and constrained refinement |
| $\Delta\rangle_{max}$, $\Delta\rangle_{min}$ (e Å$^{-3}$) | 0.39, −0.59 |

Data Collection: SAINT V8.40A (Bruker, 2019); data reduction: SAINT V8.40A (Bruker, 2019); program(s) used to solve structure: SHELXT 2014/5 (Sheldrick, 2014); program(s) used to refine structure: SHELXL 2018 March (Sheldrick, 2015); molecular graphics: Olex2 1.3 (Dolomanov et al., 2009); software used to prepare material for publication: Olex2 1.3 (Dolomanov et al., 2009).

Figure 11:
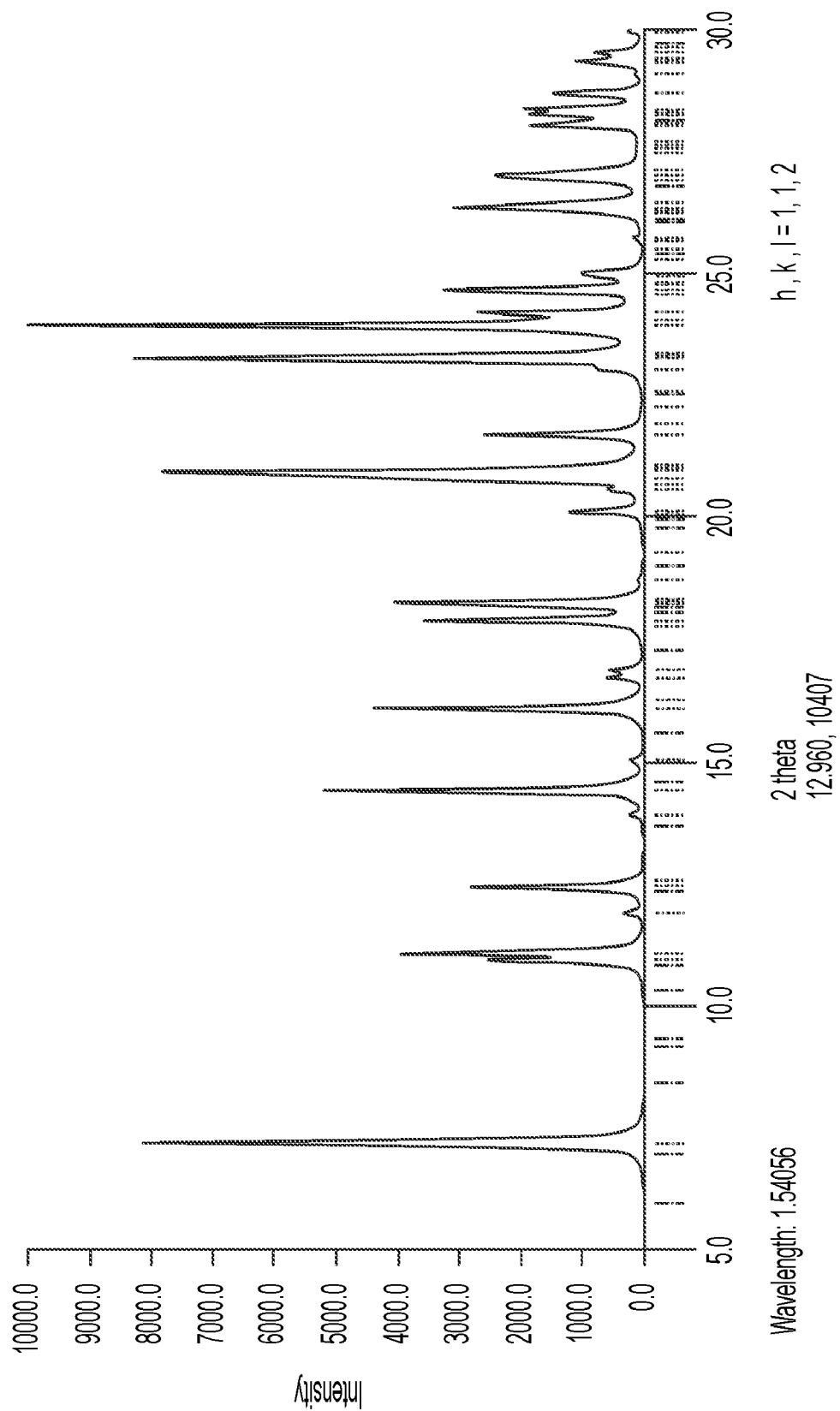
FIG. 11 depicts a simulated X-ray powder diffraction (XRPD) pattern for crystalline N—N-dibutyl-tryptamine (DBT) iodide generated from its single crystal data.
Figure 12:
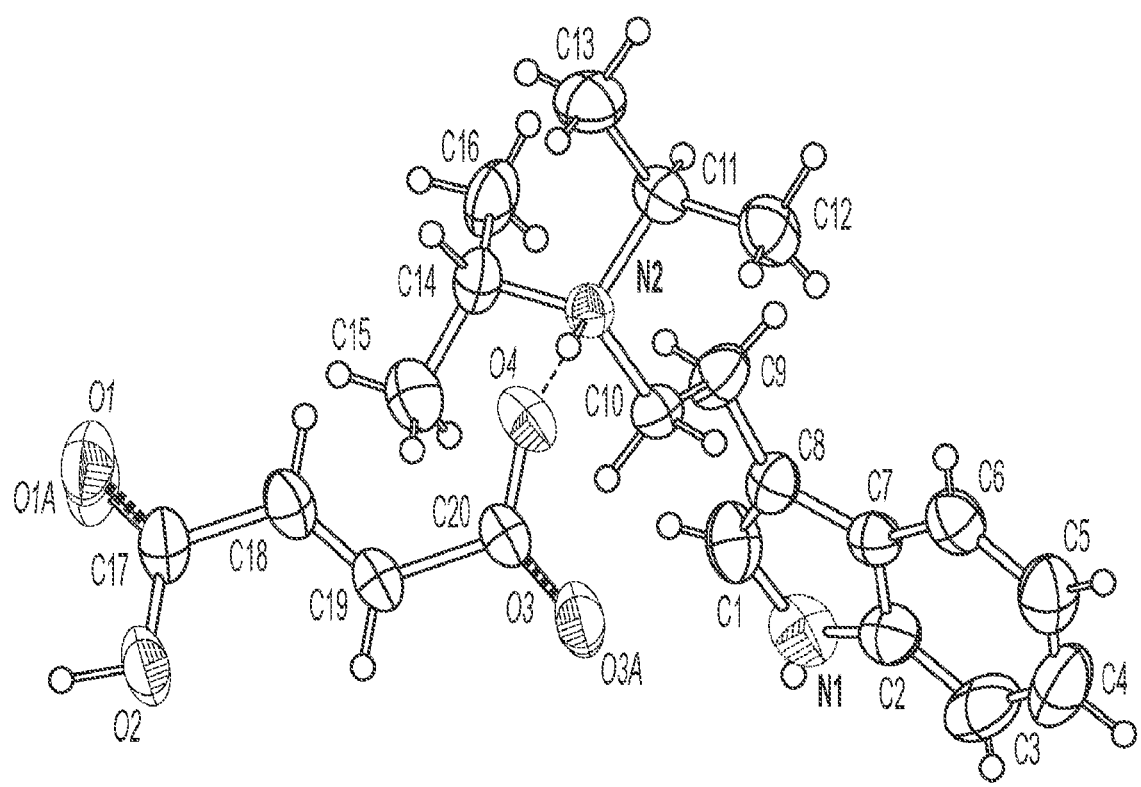
FIG. 12 depicts the molecular structure of crystalline N—N-diisopropyl-tryptamine (DiPT) hydrofumarate with atomic labelling.
Figure 13:
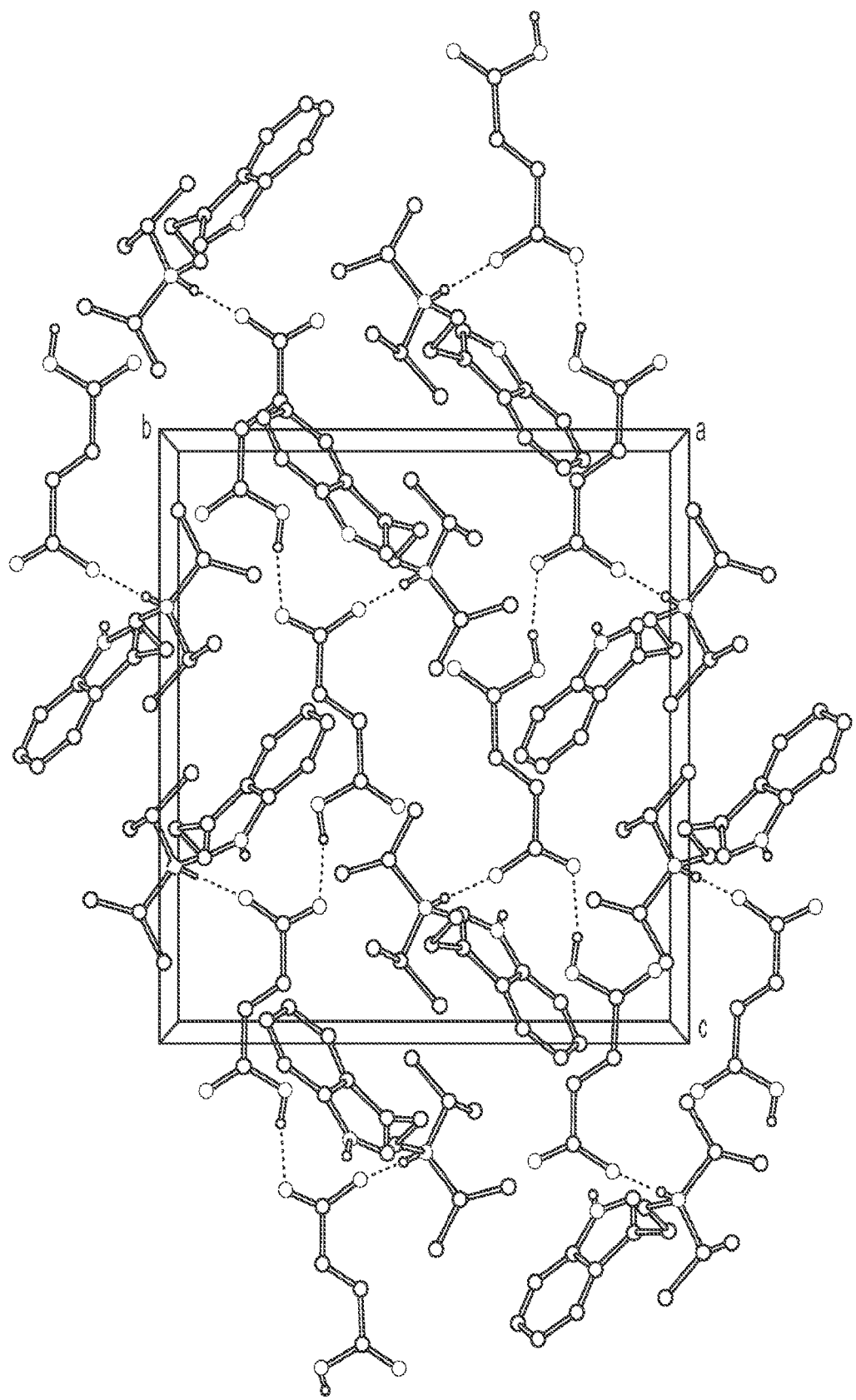
FIG. 13 shows the unit cell of crystalline N—N-diisopropyl-tryptamine (DiPT) hydrofumarate.

Simulated Powder X-ray Diffraction (PXRD) Pattern: FIG. 11 is a simulated X-ray powder diffraction (XRPD) pattern for crystalline N—N-dibutyl-tryptamine (DBT) iodide generated from its single crystal data. Table 8 lists the angles, *2θ±0.2'2θ, and d-spacing of the peaks identified in the experimental XRPD pattern of FIG. 11. The entire list of peaks, or a subset thereof, may be sufficient to characterize the cocrystal. For example, the cocrystal may be characterized by the peaks at 7.2, 14.4, and 16.1°'2θ±0.2°2θ as well as by a XRPD pattern substantially similar to FIG. 11.

TABLE 8

| d-spacing | 2 Theta (deg) | intensity |
|---|---|---|
| 12.27 | 7.2 | 113830.4 |
| 8.10 | 10.9 | 73720 |
| 7.98 | 11.1 | 126156 |
| 7.43 | 11.9 | 11537.26 |
| 7.11 | 12.4 | 119372 |
| 7.03 | 12.6 | 848.592 |
| 6.36 | 13.9 | 10904.92 |
| 6.14 | 14.4 | 298964 |
| 5.92 | 15.0 | 1067.792 |
| 5.89 | 15.0 | 12243.44 |
| 5.50 | 16.1 | 312882.8 |
| 5.44 | 16.3 | 15.29456 |
| 5.30 | 16.7 | 41496.4 |
| 5.25 | 16.9 | 40316.4 |
| 4.99 | 17.8 | 277.1656 |
| 4.95 | 17.9 | 312203.2 |
| 4.87 | 18.2 | 46.22072 |
| 4.85 | 18.3 | 370604.8 |
| 4.83 | 18.4 | 23.8396 |
| 4.73 | 18.7 | 6726.88 |
| 4.59 | 19.3 | 394.7704 |
| 4.41 | 20.1 | 144141.6 |
| 4.31 | 20.6 | 41681.84 |
| 4.29 | 20.7 | 6212.16 |
| 4.26 | 20.8 | 436156 |
| 4.24 | 21.0 | 922264 |
| 4.23 | 21.0 | 27615.84 |
| 4.21 | 21.1 | 3280.136 |
| 4.10 | 21.7 | 5521.04 |
| 4.09 | 21.7 | 345630 |
| 4.05 | 21.9 | 378.9344 |
| 3.99 | 22.3 | 2496.704 |
| 3.93 | 22.6 | 214.1272 |
| 3.85 | 23.1 | 73189.28 |
| 3.82 | 23.3 | 1225864 |
| 3.81 | 23.3 | 53887.6 |
| 3.80 | 23.4 | 9882.8 |
| 3.72 | 23.9 | 1613584 |
| 3.69 | 24.1 | 105475.2 |
| 3.67 | 24.2 | 399020.8 |
| 3.62 | 24.6 | 31706.72 |
| 3.60 | 24.7 | 538664 |
| 3.58 | 24.8 | 322.5904 |
| 3.57 | 25.0 | 94490.4 |
| 3.56 | 25.0 | 133301.2 |
| 3.52 | 25.3 | 451.1432 |

TABLE 8-continued

| d-spacing | 2 Theta (deg) | intensity |
|---|---|---|
| 3.49 | 25.5 | 2796.784 |
| 3.47 | 25.7 | 646.1976 |
| 3.46 | 25.7 | 28358.4 |
| 3.39 | 26.3 | 21790.88 |
| 3.38 | 26.3 | 212818 |
| 3.38 | 26.4 | 380268 |
| 3.37 | 26.4 | 179711.2 |
| 3.37 | 26.4 | 161576.8 |
| 3.31 | 26.9 | 191729.6 |
| 3.30 | 27.0 | 435268.8 |
| 3.28 | 27.1 | 260997.6 |
| 3.25 | 27.5 | 17226.32 |
| 3.23 | 27.6 | 2.389904 |
| 3.23 | 27.6 | 9942.8 |
| 3.22 | 27.7 | 12246.56 |
| 3.18 | 28.1 | 349707.2 |
| 3.17 | 28.1 | 129469.2 |
| 3.15 | 28.3 | 339687.2 |
| 3.15 | 28.3 | 14438.72 |
| 3.14 | 28.4 | 374284 |
| 3.11 | 28.7 | 339841.6 |
| 3.07 | 29.1 | 2601.76 |
| 3.07 | 29.1 | 17122.8 |
| 3.04 | 29.3 | 114762.4 |
| 3.04 | 29.3 | 102896.8 |
| 3.04 | 29.4 | 103504.8 |
| 3.03 | 29.4 | 19609.24 |
| 3.02 | 29.5 | 178769.6 |
| 3.01 | 29.7 | 3428.368 |
| 2.98 | 30.0 | 61798.32 |

Example 4: Crystalline N—N-diisopropyl-tryptamine (DiPT) hydrofumarate

Preparation: Single crystals of DiPT hydrofumarate suitable for X-ray diffraction analysis were obtained from the slow evaporation of a methanol/isopropanol solution of a commercial sample of DiPT hydrofumarate (ChemLogix).

Single Crystal Characterization: Crystal data, data collection and structure refinement details are summarized in Table 9.

TABLE 9

| DiPT hydrofumarate | |
| --- | --- |
| Chemical formula | $C_4H_3O_4 \cdot C_{16}H_{25}N_2$ |
| $M_r$ | 360.44 |
| Crystal system, space group | Monoclinic, $P2_1/c$ |
| Temperature (K) | 297 |
| a, b, c (Å) | 9.7954 (5), 13.6386 (6), 14.8273 (7) |
| β (°) | 101 (2) |
| V (Å$^3$) | 1944.81 (16) |
| Z | 4 |
| Radiation type | Mo Kα |
| μ (mm$^{-1}$) | 0.09 |
| Crystal size (mm) | 0.27 × 0.22 × 0.21 |
| Diffractometer | Bruker APEX-II CCD |
| Absorption correction | Multi-scan |
| | SADABS2016/2 (Bruker, 2016 February) was used for absorption correction. wR2(int) was 0.0555 before and 0.0499 after correction. The Ratio of minimum to maximum transmission is 0.9552. The λ/2 correction factor is Not present. |
| $T_{min}$, $T_{max}$ | 0.712, 0.745 |
| No. of measured, independent and observed [I > 2σ(I)] reflections | 53570, 3531, 2885 |
| $R_{int}$ | 0.044 |
| R[$F^2$ > 2σ($F^2$)], WR($F^2$), S | 0.040, 0.104, 1.05 |
| No. of reflections | 3531 |
| No. of parameters | 272 |
| No. of restraints | 42 |
| H-atom treatment | H atoms treated by a mixture of independent and constrained refinement |
| $\Delta\rangle_{max}$, $\Delta\rangle_{min}$ (e Å$^{-3}$) | 0.17, −0.14 |

Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018 March (Sheldrick, 2015); molecular graphics: Olex2 1.3 (Dolomanov et al., 2009); software used to prepare material for publication: Olex2 1.3 (Dolomanov et al., 2009).

TABLE 10

| d-spacing | 2Theta (deg) | Intensity |
| --- | --- | --- |
| 9.95 | 8.9 | 3382.904 |
| 9.62 | 9.2 | 3565.28 |
| 7.86 | 11.2 | 40.6488 |
| 7.41 | 11.9 | 1651.828 |
| 7.28 | 12.1 | 1941.468 |
| 6.82 | 13.0 | 172.4436 |
| 6.51 | 13.6 | 9262.92 |
| 6.42 | 13.8 | 11601.72 |
| 6.42 | 13.8 | 122.7988 |
| 6.18 | 14.3 | 2056.284 |
| 5.81 | 15.2 | 4652.6 |
| 5.56 | 15.9 | 10369.24 |
| 5.40 | 16.4 | 49228 |
| 5.34 | 16.6 | 3577.84 |
| 5.02 | 17.7 | 22182.72 |
| 4.98 | 17.8 | 27775.72 |
| 4.97 | 17.8 | 9396.76 |
| 4.81 | 18.4 | 54127.8 |
| 4.67 | 19.0 | 51008 |
| 4.57 | 19.4 | 22565.12 |
| 4.57 | 19.4 | 4120.76 |
| 4.53 | 19.6 | 46802 |
| 4.45 | 19.9 | 10349.84 |
| 4.42 | 20.1 | 770.338 |
| 4.34 | 20.4 | 11266.84 |
| 4.20 | 21.1 | 288.3604 |
| 4.20 | 21.1 | 4781.24 |
| 4.13 | 21.5 | 5352.88 |
| 4.11 | 21.6 | 5895.28 |
| 4.04 | 22.0 | 18942.64 |
| 3.95 | 22.5 | 156.5224 |
| 3.95 | 22.5 | 9694.4 |
| 3.93 | 22.6 | 11565.36 |
| 3.87 | 22.9 | 725.248 |
| 3.87 | 22.9 | 50420 |
| 3.87 | 23.0 | 4874.28 |
| 3.86 | 23.0 | 18405.08 |
| 3.71 | 24.0 | 68049.6 |
| 3.71 | 24.0 | 28430.44 |
| 3.70 | 24.0 | 3944.86 |
| 3.66 | 24.3 | 10979.16 |
| 3.65 | 24.3 | 20738.8 |
| 3.64 | 24.4 | 4366.06 |
| 3.64 | 24.4 | 1285.458 |
| 3.57 | 24.9 | 9.03116 |
| 3.52 | 25.3 | 10309.56 |
| 3.52 | 25.3 | 1113.684 |
| 3.47 | 25.6 | 570.596 |
| 3.46 | 25.7 | 6687.52 |
| 3.41 | 26.1 | 2203.92 |
| 3.32 | 26.8 | 37.22536 |
| 3.32 | 26.9 | 52.676 |
| 3.32 | 26.9 | 23237.08 |
| 3.32 | 26.9 | 22812.48 |
| 3.30 | 27.0 | 115.9468 |
| 3.27 | 27.3 | 40811.6 |
| 3.25 | 27.4 | 20670.32 |
| 3.21 | 27.7 | 12939.84 |
| 3.21 | 27.8 | 7986.96 |
| 3.21 | 27.8 | 13801 |
| 3.21 | 27.8 | 3110.54 |
| 3.21 | 27.8 | 16023.8 |
| 3.21 | 27.8 | 58745.2 |
| 3.18 | 28.0 | 7332.28 |
| 3.17 | 28.1 | 11668.92 |
| 3.17 | 28.1 | 3724.984 |
| 3.16 | 28.2 | 5747.78 |
| 3.13 | 28.5 | 5139.08 |
| 3.12 | 28.5 | 21870.56 |
| 3.12 | 28.6 | 5422.36 |
| 3.12 | 28.6 | 25361.76 |
| 3.10 | 28.8 | 3668.064 |

TABLE 10-continued

| d-spacing | 2Theta (deg) | Intensity |
| --- | --- | --- |
| 3.09 | 28.9 | 2589.98 |
| 3.08 | 28.9 | 1089.96 |
| 3.05 | 29.2 | 890.732 |
| 3.02 | 29.6 | 190.66 |
| 3.01 | 29.6 | 4503.96 |

REFERENCES

Ascic, E., Hansen, C. L., Le Quement, S. T. & Nielsen, T. E. (2012). Chem. Commun., 48, 3345-3347.
Blei, F., Dörner, S., Fricke, J., Baldeweg, F., Trottmann, F., Komor, A., Meyer, F., Hertweck, C. & Hoffmeister, D. (2020). Chem. Eur. J., 26, 729-734.
Brandt, S. D., Freeman, S., Fleet, I. A. & Alder, J. F. (2005b). Analyst, 130, 1258-1262.
Brandt, S. D., Freeman, S., Fleet, I. A., McGagh, P. & Alder, J. F. (2005a). Analyst, 130, 330-344.
Bruker (2018). APEX3, SAINT, and SADABS. Bruker AXS Inc., Madison, Wisconsin, USA.
Cameron, L P. & Olson, D. E. (2018). ACS Chem. Neurosci., 9, 2344-2357.
Dolomanov, O. V., Bourhis, L J., Gildea, R. J., Howard, J. A. K. & Puschmann, H. (2009). J. Appl. Cryst. 42, 339-341.
Jimenez-Garrido, D. F., G6mez-Sousa, M., Ona, G., Dos Santos, R. G., Hallak, J. E. C., Alcdzar-C6rcoles, M. A. & Bouso, J. C. (2020). Sci. Rep. 10, 4075.
Johnson, M. W., Hendricks, P. S., Barrett, F. S. & Griffiths, R. R. (2019). Pharmacol. Therapeut. 197, 83-102.
Sheldrick, G. M. (2015a). Acta Cryst. A71, 3-8.
Sheldrick, G. M. (2015b). Acta Cryst. C71, 3-8.
Sherwood, A. M., Halberstadt, A. L., Klein, A. K., McCorvy, J. D., Kaylo, K. W., Kargbo, R. B. & Meisenheimer, P. (2020). J. Nat. Prod. 83, 461-467.
Shulgin, A. T. & Shulgin, A. (2016). TiKHAL: The Continuation. Isomerdesign. Available at:http://isomerdesign.com/PiHKAL/read.php?domain=tk&id=56. Accessed 19 Mar. 2020.

The claimed invention is:

1. Crystalline N-ethyl-N-propyl-tryptamine (EPT) hydrofumarate characterized by at least one of:
   a monoclinic, $P2_1$ crystal system space group at a temperature of about 297 K;
   unit cell dimensions a=74839(8) Å, b=14.1752(14) Å, c=9.6461(10) Å, α=90°, β=110.537 (3)°, and y=90° at a temperature of about 297 K;
   an x-ray powder diffraction (XRPD) pattern substantially similar to FIG. 4; and
   an x-ray powder diffraction (XRPD) pattern having at least two peaks selected from peaks 11.6, 15.9 and 21.2°2θ±0.2°2θ.

2. Crystalline N-methyl-N-allyl-tryptamine (MALT) hydrofumarate characterized by at least one of:
   an orthorhombic, $P2_12_12$ crystal system space group at a temperature of about 297 K;
   unit cell dimensions a=7.9845 (7)Å, b=8.5641(6)Å, c=25.649 (2)Å, α=90°, β=90', and y=90° at a temperature of about 297 K;
   an x-ray powder diffraction (XRPD) pattern substantially similar to FIG. 8;
   an x-ray powder diffraction (XRPD) pattern having at least two peaks selected from peaks 11.6, 13.0, 13.8, 16.6 and 18.3°2θ±0.2°2θ; and
   an x-ray powder diffraction (XRPD) pattern having at least three peaks selected from peaks 11.6, 13.0, 13.8, 16.6 and 18.3°2θ±0.2°2θ.

3. Crystalline N,N-dibutyl-tryptamine (DBT) iodide characterized by at least one of:
   an orthorhombic, Pbca crystal system space group at a temperature of about 273 K;
   unit cell dimensions a=10.506 (2)Å, b=14.860 (3)Å, c=24.540 (5)Å at a temperature of about 273 K;
   an x-ray powder diffraction (XRPD) pattern substantially similar to FIG. 11; and
   an XRPD having peaks at 7.2, 14.4 and 16.1 °2θ±0.2°2θ.

Figure 14:
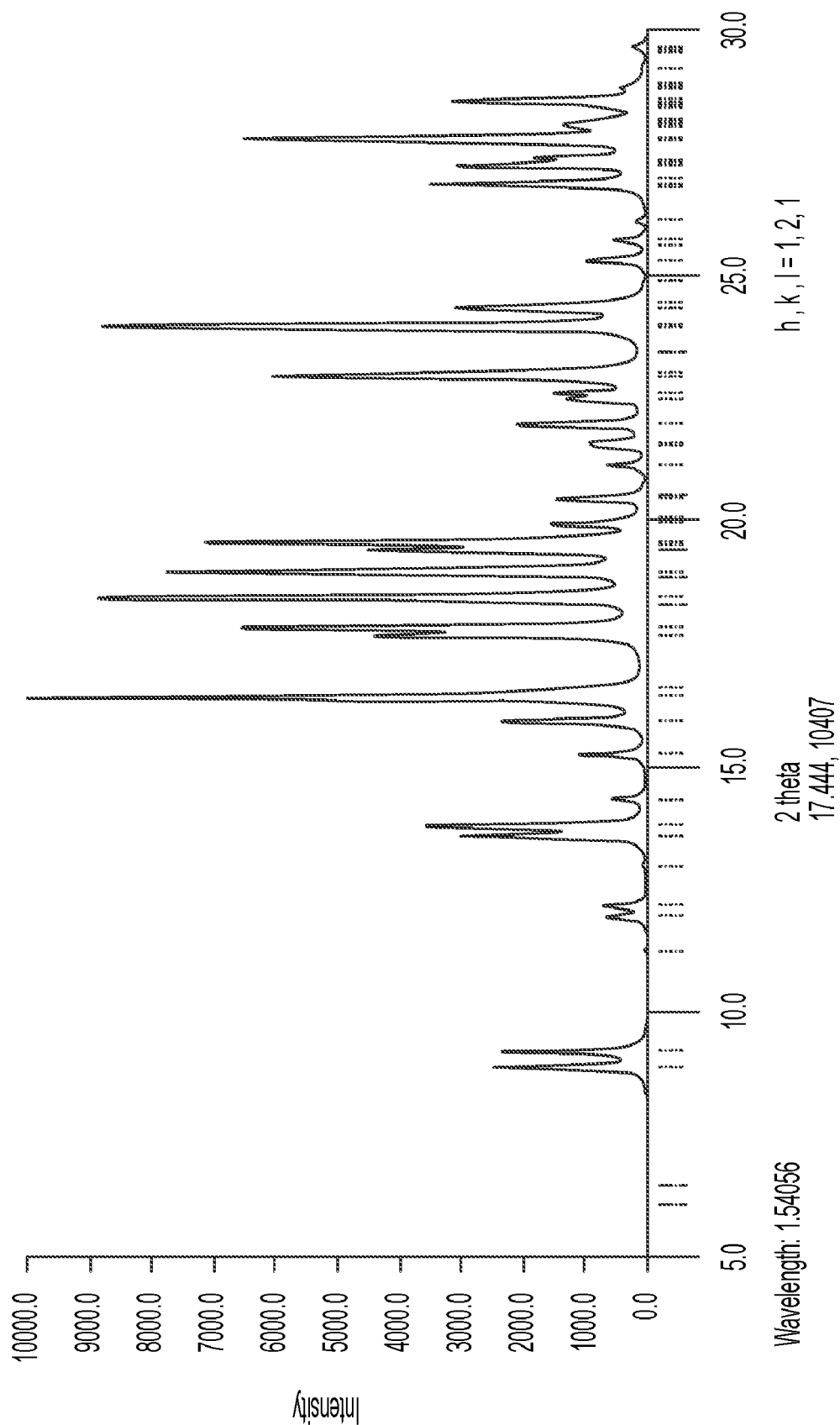
FIG. 14 depicts a simulated X-ray powder diffraction (XRPD) pattern for crystalline N—N-diisopropyl-tryptamine (DiPT) hydrofumarate generated from its single crystal data.

4. Crystalline N,N-diisopropyl-tryptamine (DiPT) hydrofumarate characterized by at least one of:
   a monoclinic, $P2_{1/c}$ crystal system space group at a temperature of about 297 K;
   unit cell dimensions α=9.7954 (5)Å, b=13.6386 (6)Å, c=14.8273 (7)Å, β=101 (2)* at a temperature of about 297 K:
   an x-ray powder diffraction (XRPD) pattern substantially similar to FIG. 14; and
   an XRPD having peaks at 16.4, 18.4, and 19.0°2θ±0,2° 2θ.

5. A composition comprising crystalline N-ethyl-N-propyl-tryptamine (EPT) hydrofumarate according to claim 1 and an excipient.

6. A composition comprising crystalline N-methyl-N-allyl-tryptamine (MALT) hydrofumarate according to claim 2 and an excipient.

7. A composition comprising crystalline N,N-dibutyl-tryptamine (DBT) iodide according to claim 3 and an excipient.

8. A composition comprising crystalline N,N-diisopropyl-tryptamine (DiPT) hydrofumarate according to claim 4 and an excipient.

* * * * *